US011692226B2

(12) United States Patent
Heimark et al.

(10) Patent No.: US 11,692,226 B2
(45) Date of Patent: Jul. 4, 2023

(54) GENOTYPING OF SNPS TO STRATIFY CANCER RISK

(71) Applicants: ARIZONA BOARD OF REGENTS ON BEHALF OF THE UNIVERSITY OF ARIZONA, Tucson, AZ (US); ARIZONA BOARD OF REGENTS ON BEHALF OF THE NORTHERN ARIZONA UNIVERSITY, Flagstaff, AZ (US)

(72) Inventors: Ronald L. Heimark, Tucson, AZ (US); Kelsey Guest, Tucson, AZ (US); Jason Wilder, Flagstaff, AZ (US); Virginia Ware, Flagstaff, AZ (US); Christina Laukaitis, Tucson, AZ (US)

(73) Assignees: ARIZONA BOARD OF REGENTS ON BEHALF OF THE UNIVERSITY OF ARIZONA, Tucson, AZ (US); ARIZONA BOARD OF REGENTS ON BEHALF OF THE NORTHERN ARIZONA UNIVERSITY, Flagstaff, AZ (US)

(*) Notice: Subject to any disclaimer, the term of this patent is extended or adjusted under 35 U.S.C. 154(b) by 217 days.

(21) Appl. No.: 16/635,233

(22) PCT Filed: Jul. 31, 2018

(86) PCT No.: PCT/US2018/044473
§ 371 (c)(1),
(2) Date: Jan. 30, 2020

(87) PCT Pub. No.: WO2019/027945
PCT Pub. Date: Feb. 7, 2019

(65) Prior Publication Data
US 2021/0102253 A1    Apr. 8, 2021

Related U.S. Application Data

(60) Provisional application No. 62/539,139, filed on Jul. 31, 2017.

(51) Int. Cl.
C12Q 1/6883 (2018.01)

(52) U.S. Cl.
CPC ..... *C12Q 1/6883* (2013.01); *C12Q 2600/156* (2013.01); *C12Q 2600/178* (2013.01)

(58) Field of Classification Search
None
See application file for complete search history.

(56) References Cited

U.S. PATENT DOCUMENTS

2009/0227533 A1    9/2009  Bader et al.

FOREIGN PATENT DOCUMENTS

WO    WO 2008/073923    6/2008
WO    WO 2013/170215    11/2013

OTHER PUBLICATIONS

Graveel (Breast Cancer: Targets and Therapy 2015:7 pp. 59-79).*
Zhang (PNAS Aug. 16, 2011 vol. 108 No. 33 pp. 13653-13658).*
Hu (Am J Respir Crit Care Med vol. 183 pp. 641-648, 2011).*
DbSNP record for rs13136737 (created with build 121 on Apr. 5, 2004).*
Mitchell (Frontiers in Genetics Apr. 2014 vol. 5 Article 95 pp. 1-7).*
NCBI dbSNP record for rs143664576 (NCBI Assay ID ss342199236 entered Mar. 25, 2011).*
Al Safar (Appl Microbiol Biotechnol 2011 89:807-815).*
DbGAP Study Accession phs000306.v4.p1 Release date Apr. 17, 2014 and accessed online at http://www.ncbi.nlm.nih.gov/projects/gap/cgi-bin/study.cgi?study_id=phs000306.v4.p1.*
Dunn (Seminars in Oncology Nursing vol. 27 No. 4 Nov. 2011 pp. 241-250).*
Al Olama, AA, et al., A meta-analysis of 87,040 individuals identifies 23 new susceptibility loci for prostate cancer. Nat Genet 2014;46:1103-9.
Al-Alem, U. et al., Association of Genetic Ancestry with Breast Cancer in Ethnically Diverse Women from Chicago. PloS one 2014, 9, e112916.
Ambs, S, et al., Genomic profiling of microRNA and mRNA reveals deregulated microRNA expression in prostate cancer. Cancer Res 2008;68:6162-70.
Anokye-Danso, F, et al., How microRNAs facilitate reprogramming to pluripotency. J Cell Sci 2012;125:4179-87.
Arabkheradmand, A et al., Down-regulated microRNA-124 expressionas predictive biomarker and its prognostic significance with clinicopathological features in breast cancer patients. Diagnostic pathology 2015, 10, 178.
Auyeung, VC, et al., Beyond secondary structure: primary-sequence determinants license pri-miRNA hairpins for processing. Cell 2013;152:844-58.
Axlund, SD, et al., HOXC8 Inhibits Androgen Receptor Signaling in Human Prostate Cancer Cells by Inhibiting SRC-3 Recruitment to Direct Androgen Target Genes. Mol Cancer Res 2010;8:1643-55.
Barroso-Del Jesus, A, et al., Embryonic Stem Cell-Specific miR302-367 Cluster: Human Gene Structure and Functional Characterization of Its Core Promoter. Mol Cell Biol 2008;28:6609-19.
Barroso-Del Jesus, A, et al., The miR-302-367 cluster as a potential stemness regulator in ESCs. Cell Cycle 2009;8:394-8.
Belair, CD, et al., DGCR8 is essential for tumor progression following PTEN loss in the prostate. EMBO Rep 2015;16:1219-32.
Bensen, JT, et al., Genetic polymorphism and prostate cancer aggressiveness: A case-only study of 1536 GWAS and candidate SNPs in African Americans and European Americans. Prostate 2013;73:11-22.
Berndt, SI, et al., Two susceptibility loci identified for prostate cancer aggressiveness. Nat Commun 2015;6:6889.

(Continued)

*Primary Examiner* — Amanda Haney
(74) *Attorney, Agent, or Firm* — Casimir Jones, S.C.; Tanya A. Arenson

(57) ABSTRACT

The invention disclosed herein generally relates to genotyping one or more single nucleotide polymorphisms (SNPs) to stratify cancer risk and/or prognosis.

6 Claims, 9 Drawing Sheets
Specification includes a Sequence Listing.

(56) References Cited

OTHER PUBLICATIONS

Bettin, A, et al., Gene expression profiling of prostate cancer-associated genes identifies fibromodulin as potential novel biomarker for prostate cancer. Int J Biol Markers 2016;31:e153-e162.
Bilir, B, et al., SOX4 Is Essential for Prostate Tumorigenesis Initiated by PTEN Ablation. Cancer Res 2016;76:1112-21.
Bourguignon, LY, et al., Hyaluronan-CD44v3 Interaction with Oct4-Sox2-Nanog Promotes miR-302 Expression Leading to Self-renewal, Clonal Formation, and Cisplatin Resistance in Cancer Stem Cells from Head and Neck Squamous Cell Carcinoma. J Biol Chem 2012;287:32800-24.
Chae, Y.S. et al., Functional polymorphism in the MicroRNA-367 binding site as a prognostic factor for colonic cancer. Anticancer Res 2013, 33, 513-519.
Chang, YL, et al., MicroRNA-7 inhibits the sternness of prostate cancer stem-like cells and tumorigenesis by repressing KLF4/PI3K/Akt/p21 pathway. Oncotarget 2015;6:24017-31.
Chen, L, et al., Evolutionary conservation and function of the human embryonic stem cell specific miR-302/367 cluster. Comp Biochem Physiol Part D Genomics Proteomics 2015;16:83-98.
Chen, M.S., Jr et al., Twenty Years Post-NIH Revitalization Act: Renewing the Case for Enhancing Minority Participation in Cancer Clinical Trials. Cancer 2014, 120 Suppl 7, 1091-1096.
Chiosea, S, et al., Up-Regulation of Dicer, a Component of the MicroRNA Machinery, in Prostate Adenocarcinoma. Am J Pathol 2006;169:1812-20.
Dang, J.H. et al., Engaging diverse populations about biospecimen donation for cancer research. Journal of community genetics 2014, 5, 313-327.
Dmitriev, AA, et al., Identification of Novel Epigenetic Markers of Prostate Cancer by NotI-Microarray Analysis. Dis Markers 2015;2015:241301.
Dong, L.L. et al., Decreased expression of microRNA-124 is an independent unfavorable prognostic factor for patients with breast cancer. Diagnostic pathology 2015, 10, 45.
Fang, YX, et al., Roles of microRNAs during prostatic tumorigenesis and tumor progression. Oncogene 2014;33:135-47.
Goodall, ML, et al., The Autophagy Machinery Controls Cell Death Switching between Apoptosis and Necroptosis. Dev Cell 2016;37:337-49.
Greer Card, DA, et al., Oct4/Sox2-Regulated miR-302 Targets Cyclin D1 in Human Embryonic Stem Cells. Mol Cell Biol 2008;28:6426-38.
Guo et al. "miR-302/367/LATS2/YAP pathway is essential for prostate tumor-propagating cells . . ." Oncogene, Jul. 24, 2017, vol. 36, No. 45, pp. 6336-6347.
Han, J, et al., Molecular Basis for the Recognition of Primary microRNAs by the Drosha-DGCR8 Complex. Cell 2006;125:887-901.
He, BS, et al., Evaluation the susceptibility of five polymorphisms in microRNA-binding sites to female breast cancer risk in Chinese population. Gene 2015;573:160-5.
Hemminki, K. Familial risk and familial survival in prostate cancer. World J Urol 2012;30:143-8.
Horiguchi, A, et al., Inactivation of the NF2 Tumor Suppressor Protein Merlin in DU145 ProstateCancerCells. Prostate 2008;68:975-84.
Hu et al. "Genetic polymorphisms in the precursor MicroRNA flanking region and non-small cell lung cancer survival" Am J Respi Crit Care Med, Oct. 2010, vol. 183, No. 5, pp. 641-648.
Hu, S, et al., MicroRNA-302 Increases Reprogramming Efficiency via Repression of NR2F2. Stem Cells 2013;31:259-68.
International Search Report & Written Opinion, International Patent Application No. PCT/US2018/044473, dated Nov. 1, 2018, 15 pages.
Jacob, S, et al., Androgen receptor as a regulator of ZEB2 expression and its implications in epithelial-to-mesenchymal transition in prostate cancer. Endocr Relat Cancer 2014;21:473-86.

Jeter, CR, et al., Functional Evidence that the Self-Renewal Gene NANOG Regulates Human Tumor Development. Stem Cells 2009;27:993-1005.
Johansson, JE, et al., Natural History of Early, Localized Prostate Cancer. JAMA 2004;291:2713-9.
Kikugawa, T, et al., PLZF Regulates Pbx1 Transcription and Pbx1 HoxC8 Complex Leads to Androgen-Independent ProstateCancer Proliferation. Prostate 2006;66:1092-9.
Kregel, S, et al. Sox2 is an androgen receptor-repressed gene that promotes castration-resistant prostate cancer. PLoS One 2013;8:e53701.
Lehrer et al. "Serum thyroid-stimulating hormone is elevated in men with Gleason 8 prostate cancer" BJU International, Jul. 24, 2005, vol. 96, pp. 328-329.
Li, H, et al., Prostate Cancer Stem Cells and Their Potential Roles in Metastasis. J Surg Oncol 2011;103:558-62.
Li, HL, et al., miR-302 regulates pluripotency, teratoma formation and differentiation in stem cells via an AKT1/OCT4-dependent manner. Cell Death Dis 2016;7:e2078.
Li, J, et al., PTEN, a Putative Protein Tyrosine Phosphatase Gene Mutated in Human Brain, Breast, and Prostate Cancer. Science 1997;275:1943-7.
Li, X, et al., Comparative mRNA and microRNA Expression Profiling of Three Genitourinary Cancers Reveals Common Hallmarks and Cancer-Specific Molecular Events. PLoS One 2011;6:e22570.
Liang, Z, et al., MicroRNA-302 Replacement Therapy Sensitizes Breast Cancer Cells to Ionizing Radiation. Pharm Res 2013;30:1008-16.
Lin, SL, et al., Mir-302 reprograms human skin cancer cells into a pluripotent ES-cell-like state. RNA 2008;14:2115-24.
Lin, Y, et al., Snail1-dependent control of embryonic stem cell pluripotency and lineage commitment. Nat Commun 2014;5:3070.
Lindstrom, LS, et al., Familial concordance in cancer survival: a Swedish population-based study. Lancet Oncol 2007;8:1001-6.
Liu, C, et al., Identification of miR-34a as a potent inhibitor of prostate cancer progenitor cells and metastasis by directly repressing CD44. Nat Med 2011;17:211-5.
Mahapatra, S, et al., Global Methylation Profiling for Risk Prediction of Prostate Cancer. Clin Cancer Res 2012;18:2882-95).
Malinowski et al. "Genetic Variants Associated with Serum Thyroid Stimulating Hormone (TSH) Levels in European Americans . . ." PLoS One, Dec. 2014, vol. 9, Iss. 12, e11130, pp. 1-21.
Marson, A, et al., Connecting microRNA genes to the core transcriptional regulatory circuitry of embryonic stem cells. Cell 2008;134:521-33.
Martinez, M., et al., Comparative study of breast cancer in Mexican and Mexican-American women. Health Care Law Mon 2010, 2, 1040-1048.
Martinez, M.E. et al., Association Between Parity and Obesity in Mexican and Mexican-American Women: Findings from the Ella Binational Breast Cancer Study. Journal of immigrant and minority health / Center for Minority Public Health 2013, 15, 234-243.
Mori, M, et al., Hippo signaling regulates Microprocessor and links cell density dependent miRNA biogenesis to cancer. Cell 2014;156:893-906.
Murray, MJ, et al., Identification of MicroRNAs From the miR-371 373 and miR-302 Clusters as Potential Serum Biomarkers of Malignant Germ Cell Tumors. Am J Clin Pathol 2011;135:119-25.
Nodora, J.N. et al., Development and Psychometric Assessment of the Measure of Globalization Influence on Health Risk (MGIHR) Among Mexican Women with Breast Cancer. J Immigr Minor Health. Aug. 2015;17(4):1025-32.
Patrawala, L, et al., Highly purified CD44þ prostate cancer cells from xenograft human tumors are enriched in tumorigenic and metastatic progenitor cells. Oncogene 2006;25:1696-708.
Peng, C, et al., A polymorphism at the microRNA binding site in the 3' untranslated region of RYR3 is associated with outcome in hepatocellular carcinoma. Onco Targets Ther 2015;8:2075-.
Poliseno, L, et al., Identification of the miR-106b~25 MicroRNA Cluster as a Proto-Oncogenic PTEN-Targeting Intron That Cooperates with Its Host Gene MCM7 in Transformation. Sci Signal 2010;3:ra29.

(56) References Cited

OTHER PUBLICATIONS

Pound, CR, et al., Identification of the miR-106b~25 MicroRNA Cluster as a Proto-Oncogenic PTEN-argeting Intron That Cooperates with Its Host Gene MCM7 in Transformation. JAMA 1999;281:1591-7.

Rosa, A, et al., A regulatory circuitry comprised of miR-302 and the transcription factors OCT4 and NR2F2 regulates human embryonic stem cell differentiation. EMBO J 2011;30:237-48.

Ryan, BM, et al., Genetic variation in microRNA networks: the implications for cancer research. Nat Rev Cancer 2010; 10:389-402.

Schaid, DJ, et al., Pooled genome linkage scan of aggressive prostate cancer: results from the International Consortium for Prostate Cancer Genetics. Hum Genet 2006;120:471-85.

Shen, MM, et al., Molecular genetics of prostate cancer: new prospects for old challenges. Genes Dev 2010;24:1967-2000.

Siegel, RL, et al., Cancer Statistics, 2016. CA Cancer J Clin 2016;66:7-30.

Society, A.C. Cancer facts & figures for hispanics/latinos 2012-2014.; Atlanta, GA, 2012.

Srivastava, A, et al., MicroRNA Profiling in Prostate Cancer—The Diagnostic Potential of Urinary miR-205 and miR-214. PLoS One 2013;8:e76994.

Ss277878916, NCBI dbSNP, Dec. 16, 2010, Ref SNP(rs#) rs13136737, pp. 1-2. Retrieved from Internet: <www.ncbi.nlm.nih/gov/projects/SNP/snp_ss.cgi?subsnp_id=277878916> Oct. 10, 2018.

Ss464009870, NCBI dbSNP, Jul. 20, 2011, RefSNP(rs#) rs186709718, pp. 1-2, Retrieved from the internet: <www.ncbi.nlm.nih.gov/projects/SNP/snp_ss.cgi?subsnp_id=464009870> on Oct. 10, 2018.

Subramanyam, D, et al., Multiple targets of miR-302 and miR-372 promote reprogramming of human fibroblasts to induced pluripotent stem cells. Nat Biotechnol 2011;29:443-8.

Takahashi, K, et al., Induction of Pluripotent Stem Cells from Adult Human Fibroblasts by Defined Factors. Cell 2007;131:861-72.

Takayama, K, et al., Integrative Analysis of FOXP1 Function Reveals a Tumor-Suppressive Effect in Prostate Cancer. Mol Endocrinol 2014;28:2012-24.

Tian, Y, et al., A microRNA-Hippo pathway that promotes cardiomyocyte proliferation and cardiac regeneration in mice. Sci Transl Med 2015;7:279ra38.

Tian, Y, et al., Regulation of lung endoderm progenitor cell behavior by miR302/367. Development 2011;138:1235-45.

Visvader, JE, et al., Cancer stem cells in solid tumours: accumulating evidence and unresolved questions. Nat Rev Cancer 2008;8:755-68.

Volinia, S, et al., Pluripotent Stem Cell miRNAs and Metastasis in Invasive Breast Cancer. J Natl Cancer Inst 2014;106.

Wang, GC, et al., MiR-367negativelyregulatesapoptosisinducedby adriamycininosteosarcomacellsbytargetingKLF4. J Bone Oncol 2016;5:51-6.

Wang, S, et al., Prostate-specific deletion of the murine Pten tumor suppressor gene leads to metastatic prostate cancer. Cancer Cell 2003;4:209-21.

Whang, YE, et al., Inactivation of the tumor suppressor PTENyM-MAC1 in advanced human prostate cancer through loss of expression. Proc Natl Acad Sci U S A 1998;95:5246-50.

Xu, J, et al., Inherited genetic variant predisposes to aggressive but not indolent prostate cancer. Proc Natl Acad Sci U S A 2010;107:2136-40.

Xu, J, et al., miR-367 promotes the proliferation and invasion of non-small cell lung cancer via targeting FBXW7. Oncol Rep 2017;37:1052-8.

Yu, Z, et al., Aberrant allele frequencies of the SNPs located in microRNA target sites are potentially associated with human cancers. Nucleic Acids Res 2007;35:4535-41.

Zeng, Y, et al., Recognition and cleavage of primary microRNA precursors by the nuclear processing enzyme Drosha. EMBO J 2005;24:138-48.

Zhang, B, et al., A dosage-dependent pleiotropic role of Dicer in prostate cancer growth and metastasis. Oncogene 2014;33:3099-108.

Zhang, L. et al., Functional SNP in the microRNA-367 binding site in the 3'UTR of the calcium channel ryanodine receptor gene 3 (RYR3) affects breast cancer risk and calcification. Proc Natl Acad Sci U S A 2011,108, 13653-13658.

Zhu, Z, et al., miR-367 promotes epithelial-to-mesenchymal transition and invasion of pancreatic ductal adenocarcinoma cells by targeting the Smad7-TGF-b signalling pathway. Br J Cancer 2015;112:1367-75.

Zhu, Z, et al., miR-367 promotes proliferation and stem-like traits in medulloblastoma cells. Cancer Sci 2015;106:1188-95.

\* cited by examiner

GENOTYPING OF SNPS TO STRATIFY CANCER RISK

CROSS-REFERENCE TO RELATED APPLICATIONS

This application is a Section 371 U.S. national stage entry of International Patent Application No. PCT/US2018/044473, International Filing Date Jul. 31, 2018 which claims priority to and the benefit of U.S. Provisional Application No. 62/539,139, filed Jul. 31, 2017, which are hereby incorporated by reference in their entireties.

STATEMENT REGARDING FEDERALLY-SPONSORED RESEARCH

This invention was made with government support under Grant Nos. U54 CA143924 and U54 CA143925 awarded by NIH. The government has certain rights in the invention

FIELD OF THE INVENTION

The invention disclosed herein generally relates to genotyping one or more single nucleotide polymorphisms (SNPs) to stratify cancer risk, for example pertaining to discriminating between high- and low-risk prostate cancer.

BACKGROUND

Prostate cancer (PCa) represents 10.7% of the newly diagnosed cancer cases in the United States, and in 2016 there were an estimated 180,000 new PCa diagnoses and 26,000 deaths (Siegel R L, et al., 2016. CA Cancer J Clin 2016; 66:7-30). Men with low grade localized disease are generally curable, however, in some men PCa progresses to metastatic disease (Johansson J E, et al., JAMA 2004; 291:2713-9). Therapy for advanced disease utilizes androgen-deprivation approaches, but most patients eventually develop resistance to the treatment and progress to castration-resistant disease (Pound C R, et al., JAMA 1999; 281:1591-7). Significant progress has been made in identifying genes and pathways involved in prostate cancer progression to metastasis; however, understanding their roles in the biological and clinical diversity of the disease remains a challenge (Shen M M, et al., Genes Dev 2010; 24:1967-2000). PCa is clinically and biologically highly heterogeneous, and can vary from localized latent disease that does not require active treatment to aggressive disease associated with a high risk of metastasis and mortality. It is important for clinicians in management of this disease to know how aggressive a patient's cancer is. Screening for PCa with serum PSA level and other clinical indicators has been successful in early detection of many cancers, and has contributed to a lower mortality. However, some aggressive cancers are missed in PSA screening and PSA screening has also lead to over diagnosis and treatment with its own complications.

Risk factors for PCa include age, family history, race and environmental exposures. Strong evidence shows that family history (first degree relative) is a determinant of risk for a subset of cancers and suggests a genetic predisposition for PCa. There is a lack of molecular biomarkers that distinguish between nonaggressive and aggressive subsets of the disease. Commonly used to define insignificant-prostate cancers are based on pathologic assessment of the radical prostatectomy specimen (Gleason score ≤6; no Gleason 4/5 pattern; organ confined disease; and tumor volume ≤0.5 cm$^3$). Approaches used to elucidate genetic risk factors include family-based linkage analysis, genome wide association studies (GWAS) in mainly populations of European Ancestry, and pathway-based association studies. GWAS analyses have identified several single nucleotide polymorphisms (SNPs) associated with elevated risk of PCa, but very few risk loci exist for aggressive PCa.

BRIEF DESCRIPTION OF THE DRAWINGS

Those of skill in the art will understand that the drawings, described below, are for illustrative purposes only. The drawings are not intended to limit the scope of the present teachings in anyway.

SUMMARY

Figure 1:
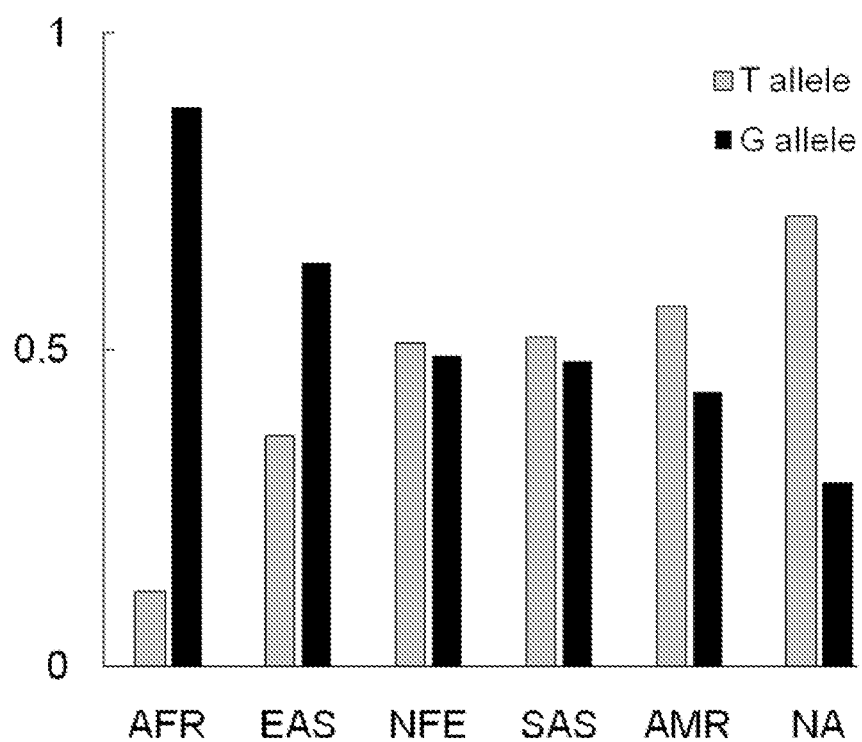
FIG. 1 depicts allele frequencies for SNP rs13136737 for 6 global populations retrieved from the ExAc database (Karczewski K J, et al., Nucleic Acids Res 2017; 45:D840-D845), as well as novel data describing Native Americans (NA); AFR=African/African Americans, EAS=East Asians, NFE=Non-Finnish Europeans, SAS=South Asians, AMR=Latinos. The Native Americans have the highest frequency of the T allele relative to other world populations. This figure demonstrates that the variant rs13136737 is common world-wide, and thus can be highly informative with respect to cancer risk in individual regardless of racial/ethnic ancestry.

Some embodiments of the invention relate to a method of determining a subject's cancer prognosis. The cancer can be correlated with the upregulation of the miR302/367 gene. The cancer can be prostate, breast, pancreatic, gastric, colorectal, germ cell, nonsmall cell lung or the like, or combinations thereof. The cancer can be prostate cancer. The method can include analyzing a sample from said subject for the presence or absence of one or more polymorphisms associated with the miR-302/367 gene and the presence or absence of the one or more polymorphisms can be indicative of the subject's cancer prognosis.

Certain embodiments provide a methods of detecting the presence of one or more polymorphisms associated with the miR-302/367 gene, comprising contacting a sample from a subject with one or more reagents for detecting the polymorphisms; and detecting the presence of the polymorphisms.

In some embodiments, the one or more polymorphisms can be within the pri-miRNA of miR-302/367. In some embodiments, the one or more polymorphisms can include rs13136737. In some embodiments, the one or more polymorphisms can include a T allele variation of rs13136737. In some embodiments, the one or more polymorphisms can be within the miR367 binding site of a miR-367 target gene. In some embodiments, the one or more polymorphisms can disrupt one or more miR-367 target sites. In some embodiments, the one or more polymorphisms can create a novel miR-367 target site. In some embodiments, the miR-367 target site can be RYR3, BCL11B, CTDSPL, F2RL1, FOXP1, HOXC8, NF2, RBBP4, SQSTM1, SOX4, or the like.

In some embodiments, the one or more polymorphisms can be one or more of: rs3738605 (SZRD1), rs17002178 (CYYR1), rs4832251 (PTCD3), rs1134256 (DQ594001), rs1044129 (RYR3) or the like.

In some embodiments, the one ore more polymorphisms can be one or more of: rs186709718 (BCL11B), rs114207812 (CTDSPL), rs770958350, rs376212863, rs376212863, rs1899860773, rs2243063; rs751458316; r3368806393-(F2RL1), rs545507911 (FoxP1), rs187964390 (HoxC8), rs558494389 (NF2), rs190184622, rs779160212 (RBBP4), rs143664576 (SQSTM1), rs562700047, rs762176006 (SOX4), rs778937405, rs748425699 (PHLPP2), rs542637158 (MAP2K4), rs754041066 (HMGA2), rs755829405 (PIP5k1c), or the like.

In some embodiments, the one or more polymorphisms can be selected from Table 4.

In some embodiments, the sample can be blood, saliva or buccal swab, or tumor tissue.

Some embodiments relate to a kit for determining a subject's risk of developing cancer and/or prognosis for cancer. The cancer can be correlated with the upregulation of the miR302/367 gene. The cancer can be prostate, breast, pancreatic, gastric, colorectal, germ cell, nonsmall cell lung or the like, or combinations thereof. The cancer can be aggressive prostate cancer. The kit can include reagents for genotyping one or more polymorphisms associated with the miR-302/367 gene.

Some embodiments relate to a method of determining a subject's risk of developing cancer. The method can include analyzing a sample from the subject for the presence or absence of one or more polymorphisms associated with the miR-302/367 gene. The presence or absence of the one or more polymorphisms can be indicative of the subject's risk of developing cancer. The cancer can be correlated with the upregulation of the miR302/367 gene. The cancer can be prostate, breast, pancreatic, gastric, colorectal, germ cell, nonsmall cell lung or the like, or combinations thereof.

Some embodiments relate to a method of determining a subject's risk of developing aggressive prostate cancer. The method can include analyzing a sample from said subject for the presence or absence of one or more polymorphisms associated with the miR-302/367 gene. The presence or absence of the one or more polymorphisms can be indicative of the subject's risk of developing aggressive prostate cancer. The aggressive prostate cancer can include metastasis.

Additional embodiments provide a method of determining a subject's risk of breast cancer, comprising analyzing a sample from the subject for the presence or absence of one or more polymorphisms at rs1044129. In some embodiments, the polymorphism is AA, AG, or GG. In some embodiments, the method further comprises detecting the presence of one or more polymorphisms at rs13136737 (e.g., GG, FT, or TT). In some embodiments, a combination of TT at rs13136737 and GG at rs1044129 is indicative of a high risk of breast cancer.

Certain embodiments provide a kit, comprising: a) a first reagent for detecting the presence of one or more polymorphisms at rs1044129; and b) a second reagent for detecting the presence of one or more polymorphisms at rs13136737.

DETAILED DESCRIPTION OF THE INVENTION

Unless otherwise noted, terms are to be understood according to conventional usage by those of ordinary skill in the relevant art.

A frequent genetic alteration in PCa is inactivation of the tumor suppressor PTEN (phosphatase and tensin homolog deleted on chromosome 10), which has a critical role in prostate oncogenesis, recurrence, and development of castration resistance (Li J, et al., Science 1997; 275:1943-7; Wang S, et al., Cancer Cell 2003; 4:209-21; Whang Y E, et al., Proc Natl Acad Sci USA 1998; 95:5246-50). MicroRNA biogenesis was recently found to be required for disease progression in conjunction with PTEN loss (Belair C D, et al., EMBO Rep 2015; 16:1219-32; Zhang B, et al., Oncogene 2014; 33:3099-108; Chiosea S, et al., Am J Pathol 2006; 169:1812-20). Deletion of one allele of PTEN occurs in 20-40% of primary human prostate cancers and ~60% of metastases. Thus, deregulated microRNA abundance can contribute to regulation of metastatic gene networks in cancer progression (Ambs S, et al., Cancer Res 2008; 68:6162-70).

MicroRNAs (miRNAs) are noncoding regulatory RNAs that function to suppress translation by binding to complementary mRNAs; this causes translational inhibition or initiates degradation of target mRNAs Cell 2009; 136:215-33). miRNAs are expressed as a primary transcript (pri-miRNAs) containing either single or multiple hairpin structures which can be processed into mature miRNA molecules Nat Rev Mol Cell Biol 2014; 15:509-24) This processing begins with the identification and excision of individual hairpin formations from within the pri-miRNA by the "Microprocessor" complex, which contains the double-stranded RNA-binding protein DGCR8 and the RNase III enzyme Drosha (Gregory R I, et al., Nature 2004; 432:235-40; Denli A M, et al., Nature 2004; 432:231-5). Microprocessor recognizes the pri-miRNA and cleaves the 5' and 3' flanking segments to generate stem-loop "pre-miRNA" structures that are exported from the nucleus via the Exportin 5 pathway (Han J, et al., Cell 2006; 125:887-901; Zeng Y, et al., EMBO J 2005; 24:138-48). In the cytoplasm the loop of the pre-miRNA is removed by the enzyme Dicer, leaving a complex of duplexed RNA ~22 nucleotides in length. Each strand of this duplexed molecule has the potential to incorporate into the RNA-induced Silencing Complex (RISC), where it will act as a mature miRNA with the capacity to down-regulate target mRNAs. Regulation of mature miRNA expression can occur via control of transcription initiation (production of pri-miRNAs) or via regulation of any of the steps of miRNA processing by various interacting cofactors.

The invention relates to an emerging miRNA locus, the miR-302/367 cluster, which lies within an intron of the protein-coding LARP7 gene (4q25) (Anokye-Danso F, et al., J Cell Sci 2012; 125:4179-87). Despite its intronic location, transcription of the cluster is under the control of a conserved independent promoter activated by the early-developmental transcription factors Oct3/4 (also known as Pou5F1), Sox2 (SRY sex determining region Y-box2) and Nanog (Barroso-delJesus A, et al., Mol Cell Biol 2008; 28:6609-19; Card D A, et al., Mol Cell Biol 2008; 28:6426-38; Marson A, et al., Cell 2008; 134:521-33) The polycistronic pri-miR-302/367 encodes five mature miRNAs loci (miR-302b, miR-302a, miR-302c, miR-302d and miR-367). Members of the miR-302 family have high sequence identity to one another, and mature-3p miRNAs have identical seed regions, indicating that they share mRNA targets. (Barroso-delJesus et al., supra) In contrast, miR-367 has a distinct seed region with little identity to the miR-302 family and likely a distinct set of mRNA targets. (Card et al., supra) Normal expression of this miRNA cluster appears limited to pluripotent embryonic stem cells, with diminished expression following cellular differentiation (Card et al., supra; Marson A, et al., Cell 2008; 134:521-33; Tian Y, et al., Development 2011; 138:1235-45). Up-regulation of the cluster has been observed in numerous cancer types, including pancreatic cancer, head and neck squamous cell carcinoma, nonsmall cell lung cancer (with higher expression correlating with poorer outcomes), malignant germ cell tumors, gastric and breast cancer stem cells (Liang Z, et al., Pharm Res 2013; 30:1008-16; Volinia S, et al., J Natl Cancer Inst 2014; 106; Zhu Z, et al., Br J Cancer 2015; 112:1367-75; Bourguignon L Y, et al., J Biol Chem 2012; 287:32800-24; Li X, et al., PLoS One 2011; 6:e22570).

The invention relates to a little-studied common genetic variant that is found within the pri-miRNA of miR-302/367, single nucleotide polymorphism (SNP) rs13136737. This site, which is variable in worldwide populations, falls between the hairpin-forming regions of miR-302d and miR-367, near the 3' end of the miRNA cluster. Studies have linked both deregulated expression and genetic variation in miRNAs to prostate cancer risk (Fang Y X, et al., Oncogene 2014; 33:135-47; Ryan B M, et al., Nat Rev Cancer 2010; 10:389-402). SNPs in miRNA genes can affect their biogenesis, processing, and/or target site binding in a variety of ways. The invention relates to how the two common alleles of the SNP rs13136737 in pri-miR-302/367 affect miRNA biogenesis and associate with prostate cancer progression.

A clinical challenge in prostate cancer (PCa) is identifying the characteristics of primary lesions that could give rise to metastatic disease so that patients receive immediate treatment. Genetic variation in microRNA genes can affect their biogenesis and/or mRNA targeting by mature miRNAs which can influence cancer susceptibility and progression. The invention relates to an under-studied genetic variant (rs13136737, G/T) that is near the 3' end of the polycistronic primary miRNA, hsa-miR-302/367, that is biofunctional with allele-specific properties. Embodiments of the invention relate to the biological effects and clinical consequences of this sequence variant in PCa.

The invention relates to experiments where the miR-302a, b,c,d/367 gene cluster which belongs to a class of embryonic stem cell miRNAs and miRNA expression in prostate cancer stem-like cells by RT-qPCR was analyzed. SNP rs13136737 genotype and its association with multiple clinicopathological characteristics were studied in PCa patient specimens drawn from discovery and validation cohorts. The invention relates to an analysis of miRNA expression in vitro and in vivo by RT-qPCR and in situ hybridization. Some embodiments of the invention relate to the analysis of miR-367 and miR-302 target mRNAs.

Embodiments of the invention relate to an analysis of the five mature miRNAs from the primary transcript following ectopic expression of the miR-302/367 G-allele and T-allele showed that biogenesis of miR-302d and miR-367 from the T-allele transcript were inefficiently processed to mature miRNAs, while there were normal levels of miR-302a/b/c. To evaluate the biofunctional consequences of germ line variation in rs13136737, a cohort of prostate cancer patients was genotyped. Embodiments of the invention relate to an association with cancer pathological stage at diagnosis as an indicator of aggressiveness. Cancer pathological stage is a measure of the extent of tumor and is used in conjunction with Gleason score, which is a histologic grade of prostate adenocarcinoma differentiation, in consideration of prognosis. Embodiments of the invention relate to an age-dependent association between rs13136737 genotype and increased risk of aggressive PCa. This was present in younger men [<65 years, OR=3.13, 95% confidence interval 1.46-7.52; p=0.003] and the association was replicated in an independent data set [OR: 1.58; 95% confidence interval 1.10-2.26; p=0.013]. The miR-302/367 cluster can be unregulated in a population of prostate cancer stem-like cells by the core pluripotency transcription factors Sox2, Oct4, and Nanog which activate the proximal promoter. Prostate tissue from genotyped cancer patients was analyzed by in situ hybridization and RT-qPCR for miR-367 and the results support an allele-specific regulatory mechanism in a subset of PCa cells.

Patients with the rs13136737 TT-allele can have an association with a more aggressive prostate cancer phenotype. This can be driven by a strong association with aggressive disease in younger men.

Some embodiments of the invention relate to genetic and functional approaches to examine the SNP, rs13136737 (G/T), in the pri-miR-302/367 gene. This polycistronic microRNA can play a role in embryonic stem cell pluripotency and self-renewal and can be expressed in prostate cancer stem-like cells, as well as cancer cells from other organ types (Bourguignon L Y, et al., J Biol Chem 2012; 287:32800-24; Li X, et al., PLoS One 2011; 6:e22570; Fang Y X, et al., Oncogene 2014; 33:135-47; Ryan B M, et al., Nat Rev Cancer 2010; 10:389-402; Yu Z, et al., Nucleic Acids Res 2007; 35:4535-41). The rs13136737 T-allele can reduce biogenesis of miR-367 and in two independent PCa study cohorts it can associate with risk of more aggressive disease. This risk association can occur in younger PCa patients. Embodiments of the invention relate to the use of SNP rs13136737 in a biomarker panel to identify individuals to guide personalized treatment decisions. Definitive biomarkers of aggressive disease can allow men diagnosed with prostate cancer an important treatment option of active surveillance. Embodiments of the invention relate to screening for SNP rs13136737 to reduce the risk of over-diagnosis of indolent disease in men.

miR-367 Gene Targets

Each microRNA has been shown to have numerous gene targets affecting pathways and these pathways are likely different in each cell type. Embodiments of the invention can include miR-367 gene targets can include: Rab23, a suppressor of hedgehog signaling, FBXW7, a subunit of the ubiquitin ligase complex, the transcription factor KLF4, and Integrin subunit alphaV.

Polymorphisms found either in miRNAs that affect biogenesis or in the miRNA-binding sites of target genes important in cancer could affect the expression of the miRNA targets and contribute to deregulated cancer progression. (Ryan et al., supra; yu et al., supra) Embodiments of the invention related to high miR-367 expression levels in numerous cancers including pancreatic cancer, head and neck squamous cell carcinoma, nonsmall cell lung cancer, gastric, breast cancer stem cells, and in prostate cancer. A common SNP in the 3'UTR of the RYR3 (Ryanodine receptor gene 3, rs1044129 (G/A), which is in the 3'UTR binding site for miR-367 (Zhang L, et al., Proc Natl Acad Sci USA 2011; 108:13653-8; Chae Y S, et al., Anticancer Res 2013; 33:513-9). miR-367 has a higher binding affinity for the rs1044129 A genotype than for the G genotype miR-367. This increases risk of breast and other cancers (Zhang L, et al., Proc Natl Acad Sci USA 2011; 108:13653-8; Chae Y S, et al., Anticancer Res 2013; 33:513-9) and decreases significantly recurrence-free survival (Peng C, et al., Onco Targets Ther 2015; 8:2075-9), however these results are not entirely consistent (He B S, et al., Gene 2015; 573:160-5).

Embodiments of the invention can relate to the RYR3 gene SNP, rs1044129 (G/A) in a mixed ethnic prostate cancer cohort.

Additional embodiments relate to the RYR3 gene SNP, rs1044129 (AA, AG, or GG) in breast cancer. In some embodiments, a combination of detecting the presence of one or more polymorphisms at rs1044129 and one or more polymorphisms at rs13136737 (e.g., GG, FT, or TT) is used to determine risk of breast cancer. In some embodiments, a combination of TT at rs13136737 and GG at rs1044129 is indicative of a high risk of breast cancer.

Embodiments of the invention relate to miR-367 target genes that contain genetic variation in the miR-367 binding site. These sites are predicted to have allele-specific repression of the miR-367 target gene. Embodiments of the invention relate to genes that have a role in prostate cancer. Embodiments of the invention relate to genes with rare SNPs that disrupt miR-367 target sites such as BCL11B (maintenance of cancer stem cells (Mahapatra S, et al., Clin Cancer Res 2012; 18:2882-95), CTDSPL (a highly mutable tumor suppressor) (Dmitriev A A, et al., Dis Markers 2015; 2015:241301), F2RL1 (association with metastatic phenotype) (Bettin A, et al., Int J Biol Markers 2016; 31:e153-e162), FOXP1 (tumor suppressor) (Dmitriev et al., supra; Takayama K, et al., Mol Endocrinol 2014; 28:2012-24), HOXC8 (androgen PCA growth) (Axlund S D, et al., Mol Cancer Res 2010; 8:1643-55; Kikugawa T, et al., Prostate 2006; 66:1092-9), NF2 (tumor suppressor) (Horiguchi A, et al., Prostate 2008; 68:975-84), RBBP4 (tumor suppressor), SQSTM1 (autophagy regulation) (Goodall M L, et al., Dev Cell 2016; 37:337-49), and SOX4 (essential tumor initiation in the absence of PTEN) (Bilir B, et al., Cancer Res 2016; 76:1112-21).

Some embodiments of the invention relate to the following four miR-367 target SNPs that are commonly variable: rs3738605 (SZRD1), rs17002178 (CYYR1), rs4832251 (PTCD3), rs1134256 (DQ594001).

Some embodiments of the invention relate to the following rare miR-367 target SNPs (Loss or Gain of target site):
rs186709718 (BCL11B) Gain
rs114207812 (CTDSPL) Loss
rs770958350; rs376212863; rs376212863; rs1899860773; rs2243063; rs751458316; r3368806393-(F2RL1) Loss
rs545507911 (FoxP1) Gain
rs187964390 (HoxC8) Gain
rs558494389 (NF2) Loss
rs190184622; rs779160212 (RBBP4) Loss
rs143664576 (SQSTM1) Gain
rs562700047, rs762176006 (SOX4) Loss
rs778937405; rs748425699 (PHLPP2) Loss
rs542637158 (MAP2K4) Loss
rs754041066 (HMGA2) Gain
rs755829405 (PIP5k1c) Loss Some embodiments of the invention relate to the following SNPs that are in miR367 target genes is provided in Table 4:

TABLE 4

| Chromosome | SNP Position | rsID | Target Gene | microRNA | Effect type |
|---|---|---|---|---|---|
| 1 | 10521016 | rs554529439 | DFFA | hsa-miR-367 | Loss |
| 1 | 16723084 | rs3738605 | C1orf144 (SZRD1) | hsa-miR-367 | Gain |
| 1 | 32951457 | rs779160212 | ZBTB8B | hsa-miR-367 | Gain |
| 1 | 33148335 | rs190184622 | RBBP4 | hsa-miR-367 | Loss |
| 1 | 33148343 | rs552503477 | RBBP4 | hsa-miR-367 | Loss |
| 1 | 89851044 | rs376434444 | GBP6 | hsa-miR-367 | Gain |
| 1 | 89851154 | rs564365943 | GBP6 | hsa-miR-367 | Loss |
| 1 | 114307316 | rs184323168 | RSBN1 | hsa-miR-367 | Loss |
| 1 | 150192954 | rs782081551 | ANP32E | hsa-miR-367 | Loss |
| 1 | 150192956 | rs782250445 | ANP32E | hsa-miR-367 | Loss |
| 1 | 154452717 | rs773793923 | SHE | hsa-miR-367 | Loss |
| 1 | 154452718 | rs531583915 | SHE | hsa-miR-367 | Loss |
| 1 | 172635006 | rs777956656 | FASLG | hsa-miR-367 | Gain |
| 1 | 184762656 | rs531695647 | FAM129A | hsa-miR-367 | Loss |
| 1 | 245008027 | rs534371083 | FAM36A | hsa-miR-367 | Loss |
| 1 | 247148990 | rs754529737 | ZNF695 | hsa-miR-367 | Loss |
| 1 | 247148991 | rs536218449 | ZNF695 | hsa-miR-367 | Loss |
| 2 | 86352177 | rs376149979 | DKFZp666K071 | hsa-miR-367 | Loss |
| 2 | 86352180 | rs547942938 | DKFZp666K071 | hsa-miR-367 | Loss |
| 2 | 86352964 | rs779541552 | DKFZp666K071 | hsa-miR-367 | Gain |
| 2 | 86366572 | rs4832251 | PTCD3 | hsa-miR-367 | Loss |
| 2 | 136540475 | rs377720171 | UBXN4 | hsa-miR-367 | Loss |
| 2 | 136540477 | rs761225773 | UBXN4 | hsa-miR-367 | Loss |
| 2 | 136540480 | rs764597151 | UBXN4 | hsa-miR-367 | |
| 2 | 136540480 | rs769848105 | UBXN4 | hsa-miR-367 | |
| 2 | 175299387 | rs541108841 | GPR155 | hsa-miR-367 | Loss |
| 2 | 175300247 | rs562071649 | GPR155 | hsa-miR-367 | Loss |
| 2 | 201845483 | rs369837241 | FAM126B | hsa-miR-367 | Loss |
| 2 | 201845716 | rs186713556 | FAM126B | hsa-miR-367 | Loss |
| 3 | 4888269 | rs778455839 | ITPR1 | hsa-miR-367 | Loss |
| 3 | 4888272 | rs749854946 | ITPR1 | hsa-miR-367 | Loss |
| 3 | 38025367 | rs114207812 | CTDSPL | hsa-miR-367 | Loss |
| 3 | 46559902 | rs750642705 | LRRC2 | hsa-miR-367 | Loss |
| 3 | 71005629 | rs545507911 | FOXP1 | hsa-miR-367 | Gain |
| 4 | 128760814 | rs866857502 | AK090904 | hsa-miR-367 | Loss |
| 4 | 128760820 | rs373440595 | AK090904 | hsa-miR-367 | Loss |
| 4 | 177251135 | rs367779602 | GPM6A | hsa-miR-367 | Gain |
| 5 | 55250653 | rs750312883 | IL6ST | hsa-miR-367 | Gain |
| 5 | 76129651 | rs770958350 | F2RL1 | hsa-miR-367 | Loss |
| 5 | 76129653 | rs376212863 | F2RL1 | hsa-miR-367 | Loss |
| 5 | 76129654 | rs189860773 | F2RL1 | hsa-miR-367 | Loss |
| 5 | 76129655 | rs2243063 | F2RL1 | hsa-miR-367 | Loss |
| 5 | 76129656 | rs751458316 | F2RL1 | hsa-miR-367 | Loss |
| 5 | 76130430 | rs368806393 | F2RL1 | hsa-miR-367 | Loss |
| 5 | 77781873 | rs549917675 | LHFPL2 | hsa-miR-367 | Loss |
| 5 | 122359330 | rs568220009 | PPIC | hsa-miR-367 | Gain |
| 5 | 175953785 | rs545191229 | RNF44 | hsa-miR-367 | Loss |
| 5 | 179264734 | rs143664576 | SQSTM1 | hsa-miR-367 | Gain |
| 6 | 21598237 | rs562700047 | uc003ndi.2 (SOX4) | hsa-miR-367 | Loss |
| 6 | 21598665 | rs762176006 | uc003ndi.2 (SOX4) | hsa-miR-367 | Loss |
| 6 | 30957148 | rs778675469 | uc003nsh.2 (MUC21) | hsa-miR-367 | Loss |
| 6 | 150047500 | rs866277742 | uc003qmz.2 (NUP43) | hsa-miR-367 | Loss |
| 6 | 150048072 | rs761240500 | uc003qmz.2 (NUP43) | hsa-miR-367 | Gain |
| 6 | 158932155 | rs549939832 | uc003qrf.2 (TULP4) | hsa-miR-367 | Loss |
| 7 | 33045031 | rs187615842 | uc011kak.1_8 (FKBP9) | hsa-miR-367 | Gain |
| 7 | 65422428 | rs1134256 | uc003tum.1 (DQ594001) | hsa-miR-367 | Loss |
| 7 | 92085938 | rs747154768 | uc011khq.1_4 (GATAD1) | hsa-miR-367 | Loss |
| 7 | 92086428 | rs567260225 | uc003ulx.1 (GATAD1) | hsa-miR-367 | Loss |
| 7 | 123324426 | rs182751703 | uc003vkz.2 (WASL) | hsa-miR-367 | Loss |
| 7 | 131173710 | rs776379731 | uc011kpl.1 (MKLN1) | hsa-miR-367 | Gain |
| 7 | 131177460 | rs112816609 | uc011kpl.1 (MKLN1) | hsa-miR-367 | Loss |
| 7 | 155101011 | rs766964761 | uc011kvu.1 (INSIG1) | hsa-miR-367 | Loss |
| 8 | 52731567 | rs62506082 | uc011ldm.1 (PCMTD1) | hsa-miR-367 | Gain |
| 8 | 52732396 | rs202202550 | uc011ldm.1 (PCMTD1) | hsa-miR-367 | Loss |
| 8 | 104411239 | rs73287908 | uc003yll.2 (SLC25A32) | hsa-miR-367 | Gain |
| 8 | 104412097 | rs192237910 | uc003yll.2 (SLC25A32) | hsa-miR-367 | Loss |
| 8 | 104412104 | rs184020953 | uc003yll.2 (SLC25A32) | hsa-miR-367 | Loss |
| 8 | 134469218 | rs555707201 | uc003yuk.2 (ST3GAL1) | hsa-miR-367 | Gain |
| 9 | 15874711 | rs374590195 | uc003zmf.1 (CCD171) | hsa-miR-367 | Loss |
| 9 | 15874717 | rs747377222 | uc003zmf.1 (CCD171) | hsa-miR-367 | Loss |
| 9 | 36211913 | rs1803193 | uc003zzc.2 (CLTA) | hsa-miR-367 | Gain |
| 9 | 72333222 | rs765449636 | uc004ahj.3 (PTAR1) | hsa-miR-367 | Loss |
| 9 | 97863069 | rs760485290 | uc004avh.2 (FANCC) | hsa-miR-367 | Loss |

TABLE 4-continued

| Chromosome | SNP Position | rsID | Target Gene | microRNA | Effect type |
|---|---|---|---|---|---|
| 10 | 6053558 | rs533020456 | IL2RA | hsa-miR-367 | Loss |
| 10 | 75008879 | rs755618712 | MRPS16 | hsa-miR-367 | Gain |
| 10 | 75009941 | rs367784695 | MRPS16 | hsa-miR-367 | Loss |
| 10 | 93809016 | rs184701525 | CPEB3 | hsa-miR-367 | Loss |
| 11 | 57467772 | rs374462812 | ZDHHC5 | hsa-miR-367 | Loss |
| 11 | 57467773 | rs531302092 | ZDHHC5 | hsa-miR-367 | Loss |
| 11 | 57471249 | rs947887 | MED19 | hsa-miR-367 | Loss |
| 12 | 54406375 | rs187964390 | HOXC8 | hsa-miR-367 | Gain |
| 12 | 54678186 | rs532880784 | HNRNPA1 | hsa-miR-367 | Gain |
| 12 | 66275625 | rs754041066 | HMGA2 | hsa-miR-367 | Gain |
| 14 | 57673412 | rs748046647 | EXOC5 | hsa-miR-367 | Loss |
| 14 | 91338391 | rs374026125 | RPS6KA5 | hsa-miR-367 | Loss |
| 14 | 93649237 | rs529132151 | MOAP1 | hsa-miR-367 | Loss |
| 14 | 99639317 | rs186709718 | BCL11B | hsa-miR-367 | Gain |
| 16 | 71674639 | rs752535125 | MARVELD3 | hsa-miR-367 | Gain |
| 16 | 71679015 | rs748425699 | PHLPP2 | hsa-miR-367 | Loss |
| 16 | 71679656 | rs778937405 | PHLPP2 | hsa-miR-367 | Loss |
| 16 | 83829516 | rs770459508 | CDH13 | hsa-miR-367 | Gain |
| 17 | 1325521 | rs752637820 | CRK | hsa-miR-367 | Gain |
| 17 | 12045089 | rs542637158 | MAP2K4 | hsa-miR-367 | Loss |
| 17 | 80441147 | rs759581102 | NARF | hsa-miR-367 | Loss |
| 19 | 3630608 | rs755829405 | PIP5K1C | hsa-miR-367 | Loss |
| 19 | 17716299 | rs534758720 | UNC13A | hsa-miR-367 | Gain |
| 19 | 39890140 | rs553103627 | MED29 | hsa-miR-367 | Loss |
| 19 | 39890974 | rs752056686 | MED29 | hsa-miR-367 | Gain |
| 19 | 44089448 | rs541423639 | IRGQ | hsa-miR-367 | Gain |
| 19 | 44091448 | rs577895720 | IRGQ | hsa-miR-367 | Loss |
| 19 | 44092506 | rsl86358359 | IRGQ | hsa-miR-367 | Gain |
| 20 | 44669741 | rs543402620 | SLC12A5 | hsa-miR-367 | Loss |
| 21 | 27839092 | rs17002178 | CYYR1 | hsa-miR-367 | Loss |
| 22 | 30090951 | rs558494389 | NF2 | hsa-miR-367 | Loss |

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Genotyping of rs13136737

The frequency of rs13136737 in worldwide populations from the ExAc database was examined (Karczewski et al., supra) this information was augmented by resequencing the miR-302/367 cluster in a panel of diverse Native American human DNA samples (n=41) representative of populations of South American, Mexican-Indian and Amerindian ancestry acquired from the Coriell Repository (Camden, N.J.). Genotypes of these Coriell samples were determined via Sanger sequencing and SNPs were confirmed via re-amplification and re-sequencing of the target.

The germline allelic frequency of SNP rs13136737 was determined from blood samples collected from consented prostatectomy patients and were provided by the University of Arizona Cancer Center (UACC) Biorepository. Informed consent was obtained from all subjects and studies were approved by local Research Ethics Committees and/or Institutional Review Boards (#06-0609-04). The total number of individuals included in this UACC discovery cohort was 133 which were collected between 2009-2013 (Table 1). Genomic DNA was extracted from blood samples and purified using the QIAamp DNA kit or from formalin fixed paraffin embedded tissue sections (QIAamp DNA FFPE Tissue kit) according to the manufacturer (Qiagen). All samples were genotyped using the TaqMan SNP Genotyping assay (Invitrogen/Thermo Fisher) for SNP rs13136737. Patient DNA samples, positive control samples of known genotype, negative controls, and duplicate samples were randomly analyzed, with 10% duplicates to test both inter- and intra-plate concordance. Samples that failed to genotype were recorded as undetermined. Both inter- and intra-plate duplicates were 100% concordant and the completion rate was >98%. To validate inferences generated from the UACC clinical discovery cohort, additional SNP genotype data and cancer phenotype data was retrieved from the dbGaP project "A Multiethnic Genome-wide Scan of Prostate Cancer" (accession: phs000306.v4.p1).

Quantitative Real Time RT-PCR (qPCR) of miR302/367 miRNAs and their Target Genes.

Analysis for primary and mature miRNA expression was carried out using Taqman miRNA assays (Invitrogen/Thermo Fisher) according to the manufacturer's protocol. Differences in relative expression were determined using the comparative Ct method described in the ABI user manual relative to RNU6 for mature miR-367, miR-302a, miR-302b, miR-302c, miR-302d. miRNA was extracted from cultured cell using the miRNeasy kit (Qiagen) and from microdissected 10 micron formalin fixed paraffin embedded (FFPE) tissue sections using the miRNeasy FFPE kit (Qiagen). cDNAs were reverse transcribed from 10 ng of total RNA of each sample using specific miRNA primers from the Taqman MicroRNA assays (Invitrogen/Thermo Fisher) and PCR products were amplified using Taqman Universal PCR Master mix (Invitrogen/Thermo Fisher). Taqman assays for pri-miR-302/367 transcript were normalized to HPRT1.

For gene expression analysis, total RNA was extracted using Qiazol (from Qiagen) and was reverse transcribed using random primers with Superscript II reverse transcriptase (Invitrogen/Thermo Fisher). Primers were designed using the Roche Universal Probe Library assay design center (www.universalprobelibrary.com) and QPCR was performed using Quanta PerfeCTaSupermix with low Rox (Quanta BioScience). Differences in expression were determined using the comparative Ct method described relative to HPRT1 as a loading control.

MicroRNA In Situ Hybridization.

5'digoxigenin-labelled LNA modified probes (Exiqon) for miR-367, and a negative control (scrambled-miRNA) were used and were also 3'digoxigenin-labelled using the Roche Oligonucleotide 3'-end labeling kit. Sections (5 micron) were deparaffinized and then hydrated with ethanol solutions to phosphate-buffered saline. Proteinase-K 5 µg/ml digestion at 37° C. for 20 min was followed by fixation with 4% p-formaldehyde and followed by acetylation according to the method Sempere et al. (Methods Mol Biol 2013; 980: 43-59). Then LNA-probes were denatured by heating to 65° C. for 4 min. Hybridization of the LNA-probes (50 nM) was carried out in at 50° C. overnight. Washes were performed at hybridization temperature with 2×SSC buffer twice and then 3 times at 0.5×SSC. Then sections were blocked with 5% BSA and alkaline phosphatase-conjugated anti-Digoxigenin (Roche) at 1:2000 was incubated overnight at 4° C. After washing, the substrate enzymatic reactions were carried out with NBT/BCIP at 30° C. Sections were counter stained with Methyl green (Vector Labs) for 1 min and then rinsed in water and mounted. Tumor regions were scored for miR-367 expression level and the percentage of positive cells determined.

Plasmid Constructs.

Each allele of the SNP rs13136737 was cloned from homozygous DNA containing either the reference or alternative allele. Amplified DNA was cloned using the TOPO® XL PCR Cloning Kit (Invitrogen/Thermo Fisher). For analysis of processing individual alleles for miR-302/367 cluster were amplified from homozygous genomic DNA with PhusionTaq and each of the alleles was cloned into pENTR1A/D vector (Invitrogen/Thermo Fisher). LR clonase II was used to subclone into pLENTI6 (Invitrogen/Thermo Fisher). Lentiviral particles were produced by transfecting the 293FT cells with the miR-302/367 G-allele or the miR-302/367-T allele constructs along with the packaging vectors. After lentiviral infection, cell lines stably expressing the miR-302/367 cluster (GG or TT alleles) or the control empty vector were selected in appropriate medium.

Cell Culture and Transfection.

DU145, PC3, RWPE1 and LNCaP prostate cells (American Type Culture Collection) and authenticated. PC3 and Du145 cells were maintained in Dulbecco's modified Eagle's/F12 medium supplemented with 10% heat inactivated fetal bovine serum (Hyclone Laboratories) and penicillin/streptomycin. RWPE1 cells were cultured with serum-free Keratinocyte Growth Media (Invitrogen/Thermo Fisher) with growth supplements, and LNCaP cells were grown in RPMI (Invitrogen/Thermo Fisher). Previously Li et al. (J Surg Oncol 2011; 103:558-62) and others (Collins A T, et al., Cancer Res 2005; 65:10946-51) have shown that a population of prostate cancer cells with high ALDH activity ($ALDH^{hi}$) are enriched in cells with tumor initiating properties.

To isolate prostate cancer stem cells that are $ALDH^{hi}$ cells, DU145 and LNCaP cells were suspended in ALDEFLUOR assay buffer containing ALDH substrate at 1 µM per $1 \times 10^6$ cells (StemCell Technologies) and incubated for 40 min at 37° C. and sorted by FACS (FACSAria III, BD Biosciences). As a negative control, diethylaminobenzaldehyde (DEAB) was added to the cell suspension before analysis. The cells were plated in prostosphere culture conditions at sub-clonal density (1,000 cells/ml) in a serum-free medium (DMEM/F12) containing 0.4% BSA, 0.2×B27 lacking Vitamin A (Invitrogen/Thermo Fisher) in the presence of 5 µg/l insulin in low attachment culture dishes. DU145 spheres were sub-cultured using trypsin, passed through a cell strainer and then resuspended in the above medium at clonal density (Rybak A P, et al., Cell Signal 2013; 25:2734-42)

For transfection of microRNA mimics, cells were plated at a density of $4 \times 10^4$ cells/cm² in individual 6-well tissue culture plates. Twenty-four hours after plating, cells were transfected with one of miR-302b or miR-367 mimics (Invitrogen/Thermo Fisher) at a concentration of 50 nM using Lipofectamine2000 (Invitrogen/Thermo Fisher) in OptiMEM (Invitrogen/Thermo Fisher). After transfection, cells were collected in Trizol (Invitrogen) and processed as described.

Antibodies and Immunoblotting.

For immunoblotting, cells were lysed in SDS sample buffer (Tran N L, et al., Am J Pathol 1999; 155:787-98) Protein concentrations were determined using the BCA assay procedure (Pierce). Thirty micrograms of total cellular protein were loaded per lane and separated by SDS-PAGE. After transfer, the nitrocellulose (Amersham), was blocked with 5% nonfat milk prior to addition of primary antibodies and followed with peroxidase-conjugated secondary antibodies. PTEN (Cell signaling clone 26H9), Akt1 (Cell Signaling clone 2H10), Akt (Cell signaling clone 40D4), Rab23 (Santa Cruz and Sigma), Sox2 (Santa Cruz), Oct4 (Cell Signaling), Bmi1, E-cadherin (BD Transduction Labs), Snail1 (Cell Signaling), βactin (Sigma). NR2F2 (R&D).

Statistical Analyses.

The association of rs13136737 genotypes in a mixed-race discovery cohort from UACC (n=133) with either severe/aggressive or non-severe prostate cancer was evaluated by estimating odds ratios (OR) and 95% confidence intervals (95% CI) using logistic regression analysis. Men were classified as either having evidence of localized disease (Stage 2=T2a, T2b, T2c) at prostatectomy or having evidence of more severe extraprostatic disease (Stage 3=T3a, T3b). ANOVA comparing the logistic regression models versus a null model was performed to verify associations between phenotype (severe and non-severe prostate cancer) and genotype (rs13136737 alleles).

To test the ability of rs13136737 genotype and other variables, including age and summed Gleason Score, to predict severity a set of logistic regression models that consider each of these factors alone and in combination as independent variables was built. The performance of these logistic regression models was assessed by calculating the area under the receiver operating characteristic curve (AUC). The goodness of fit of these logistic regression models was also assessed by ANOVA. All p values were two-sided, with p<0.05 considered the threshold of significance.

In addition to the discovery data set (UACC), data from the GENEVA Prostate Cancer study was assessed to verify the associations observed in the discovery data set (GENEVA data accessed from dbGAP, study ID: phs000306.v4.p1). This is the only publicly available dataset that contains PCa severity data coupled with rs13136737 genotype information (SNP rs13136737 is included on relatively few commercially available genotyping arrays). In the available dbGaP data study patients are grouped into "severe" and "not severe" categories (based on a Gleason Sum/Pathologic Staging composite), which is the closest parallel to our Stage 2 versus Stage 3. The odds ratios for severe versus not-severe in this sample were calculated as above.

Example 2

Frequency of rs13136737 Variant Allele in Populations

This study focusses on a poorly-known common genetic variant, rs13136737, which is found within the chromosome 4 polycistronic miRNA locus of miR-302a-d and miR-367. This locus is multiallelic (G/T/A), though the A allele was disregarded in this study because it is extremely rare (less than 0.01% globally). The remaining alleles (G/T) are present at intermediate frequency in worldwide populations and emerged as a site of interest in the present study during a sequencing survey of the miR-302/367 cluster in a panel of diverse Native American DNAs from Mexico and South America. The Native American samples examined here (n=41) differ in allele frequency at rs13136737 in comparison to other world populations by having the highest observed frequency of T (FIG. 1); the frequency of the T allele is lowest in African/African-American populations (0.117) and intermediate in Europeans, Latinos and South Asians (non-Native American data from (Karczewski et al., supra)).

Example 3

Allele Specific Processing of the miR-302/367 SNP rs13136737 to Mature miRNAs

Figure 7:
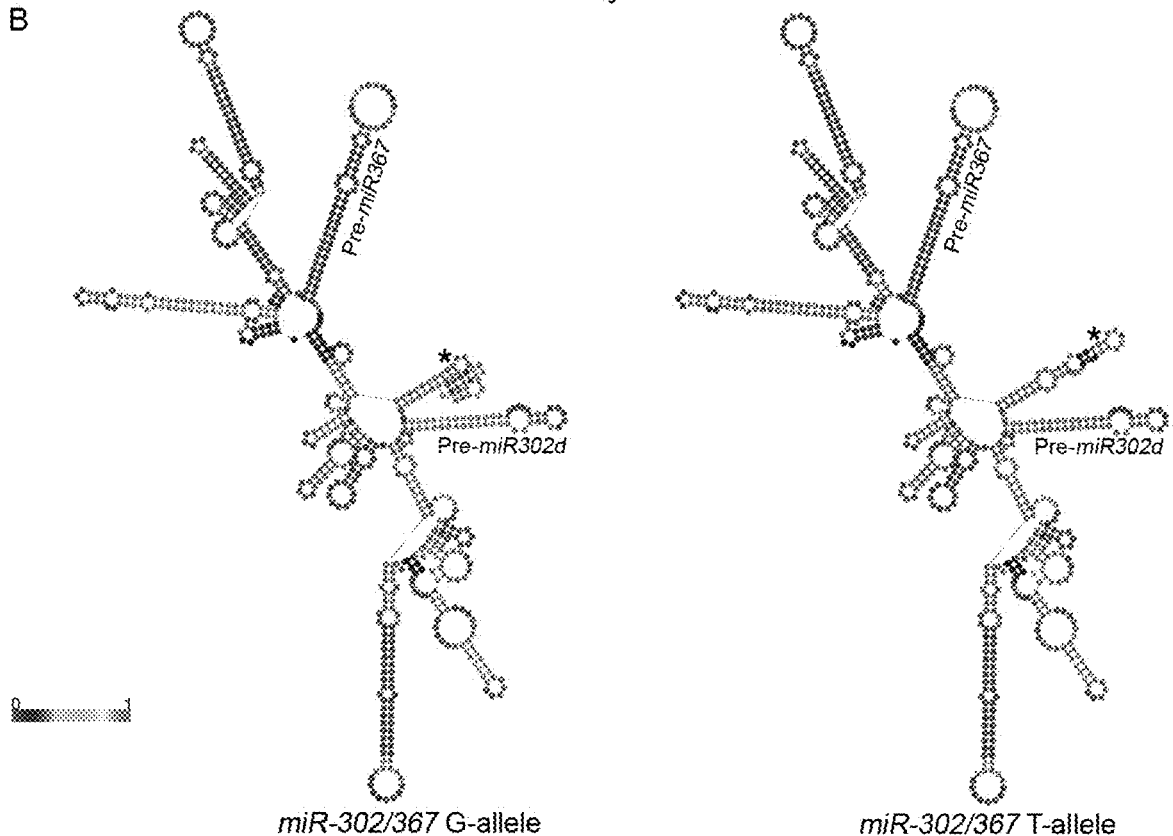
FIG. 7 depicts G/T alleles of SNP rs13136737 between pre-miR-302d and pre-miR-367. (A) Sequence of the interprecursor domain between pre-miR-302d and pre-miR-367. The SNP r513136737 (*) is located in the center of a palindromic sequence (underlined). The site of a primary sequence determinant (CNNC motif) in pri-microRNA biogenesis is boxed and is at the 5' end of the palindromic sequence. (B) For the G-allele and the T-allele secondary structure predictions of the pri-miR-302b,c,a,d/367 cluster was carried out using the RNAfold algorithm (rna.tbi univie.ac.at/cgi-bin/RNAfold.cgi).
Figure 8:
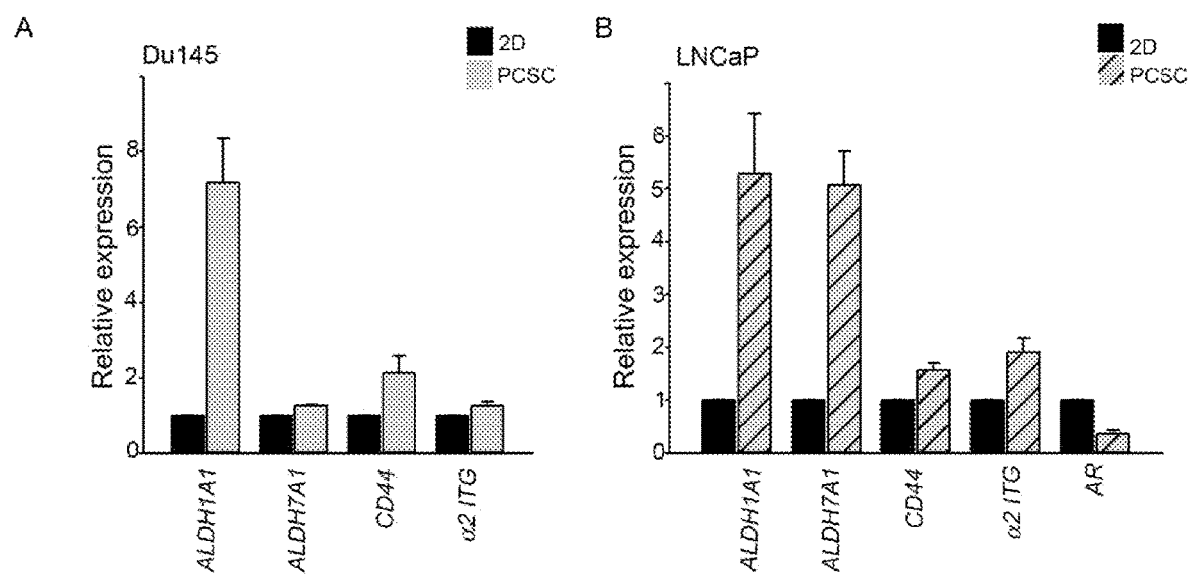
FIG. 8 depicts a characterization of the PCSC ALDH+ PCa cell subpopulation and bulk cell population of Du145 and LNCaP PCa cells. RT-qPCR analysis of transcripts in Du145 (A) and (B) LNCaP ALDH+ PCa cell subpopulations for: ALDH1A1, ALDH7A1, CD44, alpha2 integrin (α2 ITG) and androgen receptor (AR).

SNP rs13136737 falls between the hairpin-forming regions of pre-miR-302d and pre-miR-367 that are at the 3' end of the pri-miRNA transcript (FIG. 7A). The SNP is located within a complex palindromic sequence (GCAAT-TGCGTTAACG) with high potential for secondary structure formation (Chen L, et al., Comp Biochem Physiol Part D Genomics Proteomics 2015; 16:83-98). The minor T-allele of rs13136737 could impact the secondary structure of this pri-miRNA transcript with the potential to inhibit Microprocessor activity. Microprocessor recognizes the hairpin structures of the pri-miRNA through the stem loop and the stem loop single-stranded RNA junction to generate pre-miRNAs that are substrates for Dicer processing (Han J, et al., Cell 2006; 125:887-901; Zeng Y, et al., EMBO J 2005; 24:138-48). Sequences within the pri-miR-17~92 cluster have been shown to form secondary RNA conformations that restrict Microprocesssor mediated production or pre-miRNAs (Du P, et al., Cell 2015; 162:885-99). The RNA secondary structure for both alleles of pri-miR-302/367 was computationally analyzed using the RNAfold algorithm (rna.tbi.univie.ac.at/cgi-bin/RNAfold.cgi). These results indicated that the minor T-allele could regionally alter the minimal free energy to change the secondary structure of the interprecursor domain between pre-miR-302d and pre-miR-367 compared to the G-allele (FIG. 1SB).

Figure 2:
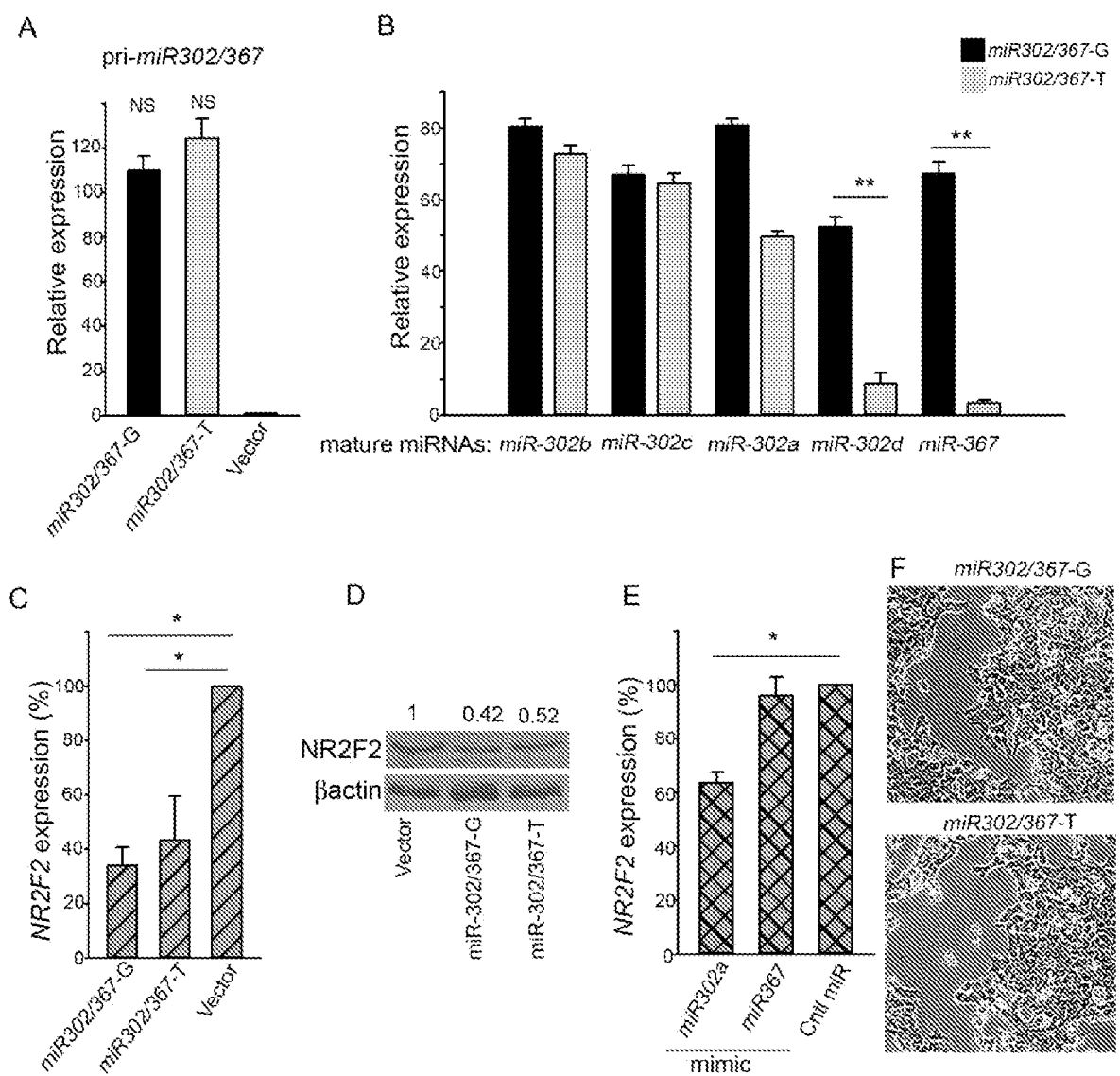
FIG. 2 depicts an analysis of lentiviral ectopic expression of the miR-302/367 G- and miR-302/367-T alleles in bulk Du145 cells. This study was undertaken to evaluate whether SNP rs13136737 is biofunctional resulting in allele-specific processing to mature microRNAs in the cluster. (A) RT-qPCR of primary transcript for cells expressing either the miR-302/367 G-allele or T-allele compared to vector only cells. (B) RT-qPCR analysis of mature miR-302/367 cluster members in cells stably expressing the G-allele or T-allele. Mature transcripts of the miR-302/367 miRNAs were analyzed by specific primers and normalized to RNU6. Data is represented as mean±SD of 3 technical replicates. (C) qPCR analysis of NR2F2 expression, a validated miR-302 target gene miR-302/367 G-allele cells or T-allele cells. (D) NR2F2 immunblot analysis of NR2F2 expression, a validated miR-302 target gene miR-302/367 G-allele cells or T-allele cells. (E) Transfection of microRNA mimics (50 nM) into Du145 cells with Lipofecatmine 2000 and analysis of NR2F2 mRNA. (E) Photomicrographs of the stable cell lines expressing either the miR-302/367G-allele or the T-allele.

Whether there is an allele specific difference for rs13136737 variants in the processing of the pri-miR-302/367 transcript to mature microRNAs was examined. The miR-302/367 gene cluster for the G- and T-alleles were each cloned into a lentiviral vector and used them to generate allele specific virus. Du145 cells were transduced at a MOI of 30 for 48 hours, and selected to develop lines stably overexpressing either the pri-miR-302/367 G- or the T-allele. The polycistronic transcript of miR-302/367 was not detected in the parental Du145 cell line by quantitative real time PCR (RT-qPCR) analysis. The miR-302/367-G and miR-302/367-T cell lines showed nearly equivalent levels of the miR-302/367 primary transcript (FIG. 2A). All five mature miRNAs of the miR-302/367 cluster were expressed in miR-302/367G-allele cells. In contrast, miR-302/367 T-allele cells expressed miR-302a, miR-302b, and miR-302c, but showed reduced levels of miR-302d and miR-367 expression (FIG. 2B). Together the results suggest that the pri-miR-302/367 T-allele in the flanking domain reduces processing of pre-miR-302d and pre-miR-367 and may be in an inhibitory RNA conformation (Zeng Y, et al., Methods Mol Biol 2006; 342:49-56). Nuclear excision of individual hairpin formations from within a polycistronicpri-miRNA is by the "Microprocessor" complex, which contains the double-stranded RNA-binding protein DGCR8 and Drosha (Han et al., supra; Zeng et al., supra; Du et al., supra). In addition, several regulatory proteins have key roles in binding and modulating miRNA biogenesis, e.g. SRp20 or DDX17 (Auyeung V C, et al., Cell 2013; 152:844-58; Mori M, et al., Cell 2014; 156:893-906). Allele-specific differential binding of accessory regulatory proteins could negatively affect the Microprocessor complex processing efficiency of pre-miR-367 from the primary transcript.

The miR-302 family members miR-302b-3p, miR-302c-3p, miR-302a-3p and miR-302d-3p have a common seed sequence targeting a set of mRNAs. The miR-302/367 T-allele reduced processing of mature miR-302d is likely to have a minimal effect on miR-302 target genes since the miR-302 dosage is reduce ~25%. The reduced expression of miR-367 has the potential to lead to a deregulated network of miR-367 targets. To examine the gene targeting by the miR-302 family in the allele specific cell lines, the transcript levels for NR2F2 (COUP-TF11) an orphan nuclear receptor that was previously reported to be targeted by miR-302 in ES cells was examined (Rosa A, et al., EMBO J 2011; 30:237-48; Hu S, et al., Stem Cells 2013; 31:259-68). The NR2F2 3'UTR has two conserved miR-302 target sites that have been validated by Rosa and Brivanlou (Rosa et al., supra). Cells expressing either the miR-302/367 G-allele or the T-allele showed greater than 60% decrease in NR2F2 mRNA expression (FIG. 2C) and western blot analysis of protein levels showed a similar decrease (FIG. 2D) and images of the transduced cells showing an adherent growth pattern (FIG. 2F). Du145 cells were transfected with miR-302a or miR-367 mimics to confirm the specific targeting of NR2F2 mRNA (FIG. 2E). NR2F2 has a dual role as a transcriptional repressor and activator which is thought to be mediated by the association with other factors. NR2F2 inhibition by miR-302 in stem cells promotes pluripotency self-renewal by positive regulation of Oct4, and NR2F2 upregulation in prostate tumors mediates a metastatic phenotype by regulating epithelial-mesenchymal transition transcriptional repressors (Rosa et al., supra; Hu et al., supra; Lin S C, et al., Nat Commun 2016; 7:11418).

Example 4

Prostate Cancer STEM-Like Cells Express the miR-302/367 Cluster

Like other solid tumor types, primary prostate tumors and cell lines contain subpopulations of cells with high capability of tumor propagation; these have been termed prostate cancer stem-like cells (PCSCs) even though they may not possess the full capabilities of stem cells in the normal prostate (Li H, et al., J Surg Oncol 2011; 103:558-62; Visvader J E, et al., Nat Rev Cancer 2008; 8:755-68). MicroRNAs refine multiple biological processes in cancer stem-like cells and for some microRNAs, including miR-34a/b, miR-200b,c, miR-141 and miR-7, their roles as tumor suppressors and oncogenes in PCSCs have been defined (Liu C, et al., Nat Med 2011; 17:211-5; Chang Y L, et al., Oncotarget 2015; 6:24017-31; Jacob S, et al., Endocr Relat Cancer 2014; 21:473-86). The core set of transcription factors Sox2, Nanog, and Oct4 (POU5F1) regulate expression of the pri-miR-302/367 cluster and are highly expressed in undifferentiated embryonic stem cells (Barroso-delJesus A, et al., Mol Cell Biol 2008; 28:6609-19; Lin S L, et al., RNA 2008; 14:2115-24; Takahashi K, et al., Cell 2007; 131:861-72). Expression profiling of miRNAs in primary PCa identified miR-367 as a differentially expressed in a discovery set of tissue samples (normal versus cancer), however there is yet little information regarding cellular expression and function of the miR-302/367 cluster (Barroso-del Jesus A, et al., Cell Cycle 2009; 8:394-8; Srivastava A, et al., PLoS One 2013; 8:e76994).

Figure 3:
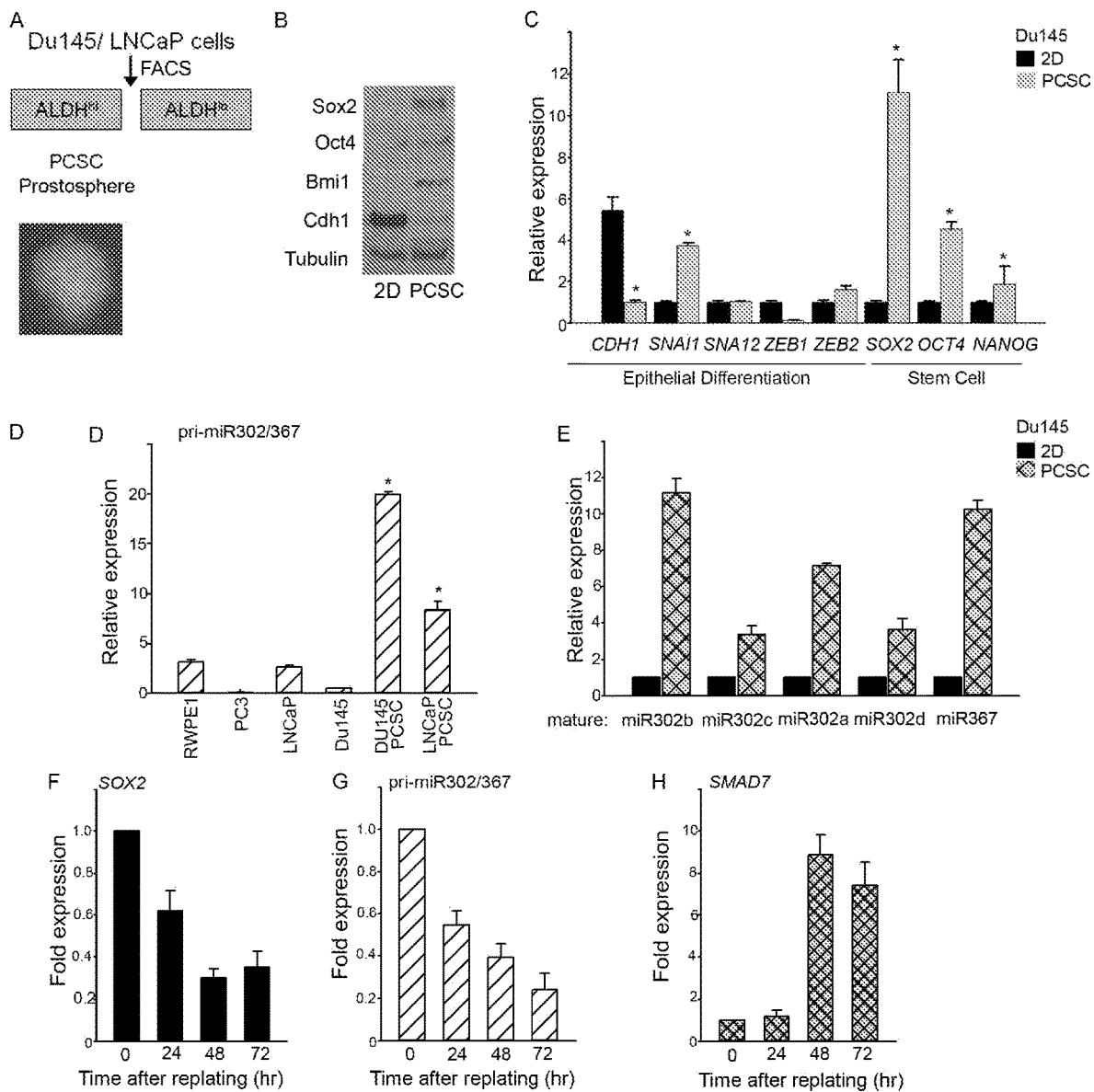
FIG. 3 depicts results of experiments involving analysis of Prostate Cancer Stem-like cells (PCSC cells) for expression and processing of the miR-302/367 microRNA cluster: (A) FACS isolation of ALDH$^{hi}$ and ALDH$^{lo}$ cells following labeling with ALDOFLUOR. (B) Western blot analysis of Du145 2D cells and PCSCs. (C) Analysis of transcript levels of epithelial differentiation and stem cell genes in PCSC and 2D cells by RT-qPCR. Note: the increase of Sox2, Nanog and Oct4 transcription factors in PCSCs. (D) Quantitative expression analysis for pri-miR-302/367 transcript in prostate cell lines: RWPE1, Du145 (rs13136737-GT), LNCaP (rs13136737-GT), PC3 (rs13136737-GG). Normalization utilized HPRT1 transcript. (E) Analysis of mature miR-302a, b,c,d/367 miRNAs by RT-qPCR. RNU6 was used for normalization. RT-qPCR showing decreased SOX2 mRNA (F), and pri-miR-302/367 (G) and SMAD7 (H) expression in PCSC prostaspheres after dissociation, replating and growth in monolayer culture containing 10% FBS.

To examine whether pri-miR-302/367 transcript expression and biogenesis in PCa cells, PCSCs was compared with cells grown in standard culture conditions. Both cell surface markers and functional strategies, such as labeling with ALDOFLOUR, have been used to isolate PCSC populations. A subpopulation of cells ALDEFLOUR$^{hi}$ was selected by FACS from AR$^-$ (androgen receptor) Du145 cells and AR$^+$ LNCaP cells and maintained in prostosphere culture conditions (PCSCs) (FIG. 3A). Du145 ALDEFLOUR$^{hi}$PCa cells have previously been shown to have tumor initiating properties in limiting dilution xenograft assays (Patrawala L, et al., Oncogene 2006; 25:1696-708). Quantitative RT-PCR analysis of ALDH$^{HI}$ Du145 PCSCs for expression of ALDH1A1 mRNA showed significantly higher expression and there was modest enrichment of integrin α2 mRNAs in PCSCs (FIG. 3B). Similar phenotypic populations of PCSCs have previously been shown to tumor initiating and propagating characteristics in NOD/SCID mouse studies. The differential expression of epithelial differentiation and stem cell transcription factors in PCSCs by RT-qPCR and immunoblotting was determined (FIGS. 3B and 3C). PCSCs clearly express protein levels of Sox2 and Oct4 in contrast to the parental Du145 cells grown in monolayer, which lack Sox2 and Oct4 expression (FIGS. 3C and D). In addition, E-cadherin (CDH1) mRNA is significantly reduced in PCSC population as was β-catenin (not shown). Increased expression of the polycomb complex protein Bmi1, a critical regulator of prostate stem cell renewal and proliferation (Lukacs R U, et al., Cell Stem Cell 2010; 7:682-93), was identified. In the PCSC cells there was increased mRNA expression of the core stem cell transcription factors SOX2, OCT4 and NANOG (FIG. 3C). PCSCs also showed increased mRNA for SNAI1, a zinc finger transcriptional repressor of E-cadherin, and the repressors ZEB1 or ZEB2, but no significant change in SNAI2, (FIG. 3C). In embryonic stem cells the transcriptional regulator Snail1 has previously been reported to have both EMT-dependent and -independent roles (Lin Y, et al., Nat Commun 2014; 5:3070). These results indicate that Du145 PCSCs, which express the pluripotency transcription factors Sox2, Oct4 and Nanog, may concomitantly have transcriptionally upregulated the pri-miR-302/367 gene cluster.

The endogenous pri-miR-302/367 expression in PCa cell lines and PCSCs was evaluated using RT-qPCR analysis. As shown in FIG. 3D, Du145 PCSCs expressed pri-miR-302/367 transcript, while it was undetectable in Du145 monolayer cells. Low levels of pri-miR-302/367 transcript were detected in RWPE1 and LNCaP cells, and LNCaP PCSCs showed enhanced pri-miR-302/367 transcripts. Genotyping of both Du145 and LNCaP cells for rs13136737 showed that they were heterozygous (G/T). The biogenesis of pri-miR-302/367 transcript into mature miRNAs in Du145 PCSCs was also evaluated. All five mature microRNAs (miR302a, b,c,d and miR-367) were found to be generated from the polycistronic cluster (FIG. 3E). Thus, Du145 and LNCaP PCSCs demonstrate enhanced expression levels of both the core set of transcription factors regulating pluripotency and self-renewal in ES cells and pri-miR-302/367 expression.

To examine whether the gene expression of SOX2 and pri-miR-302/367 in the PCSCs was reversible a replating assay was carried out (FIGS. 3F, G and H). Du145 PCSCs were collected, dissociated from prostospheres into single cells and replated in normal FBS containing growth medium on adherent culture dishes. This resulted in a significant decline in both SOX2 and pri-miR-302/367 transcripts at 24 hours. This loss continued at 48 and 72 hours suggests that miR-302/367 expression is reversible. SMAD7, a negative regulator of TGFβ signal transduction, is one of the miR-367 target genes that functions as a tumor suppressor (Zhu Z, et al., Br J Cancer 2015; 112:1367-75). With the loss of pri-miR-302/367 transcripts there was an increase in SMAD7 mRNA levels indicating a dynamic level of miRNA expression that may depend on the microenvironment (FIG. 3H).

Example 5

Figure 4:
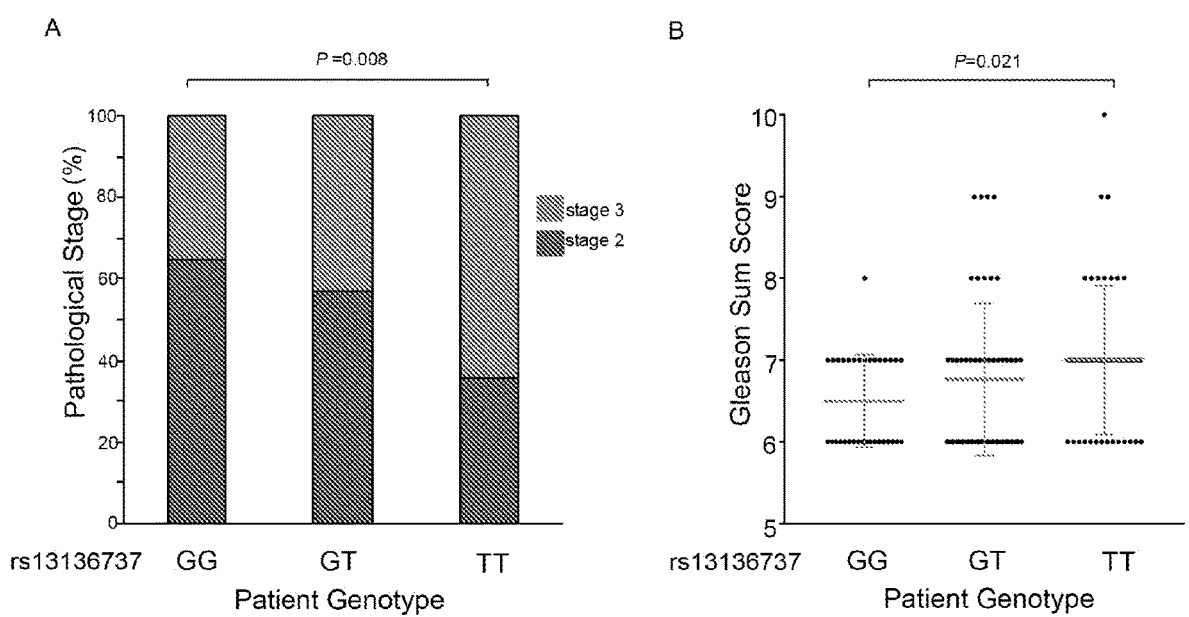
FIG. 4 depicts a genotype analysis of SNP rs13136737 (G/T) in the UACC mixed race discovery cohort of prostate cancer patients (N=131) and association with disease characteristics. (A) Pathological Stage 2 represents T2a, T2b, T2c and Stage 3 (extraprostatic penetration) represents T3a and T3b according to the American Joint Committee on Cancer Staging; there is a significant association between genotype and cancer stage. (B) Association of rs13136737 genotype with Gleason sum score; the TT genotype is associated with a significantly higher score than GG (Mann-Whitney).
Figure 9:
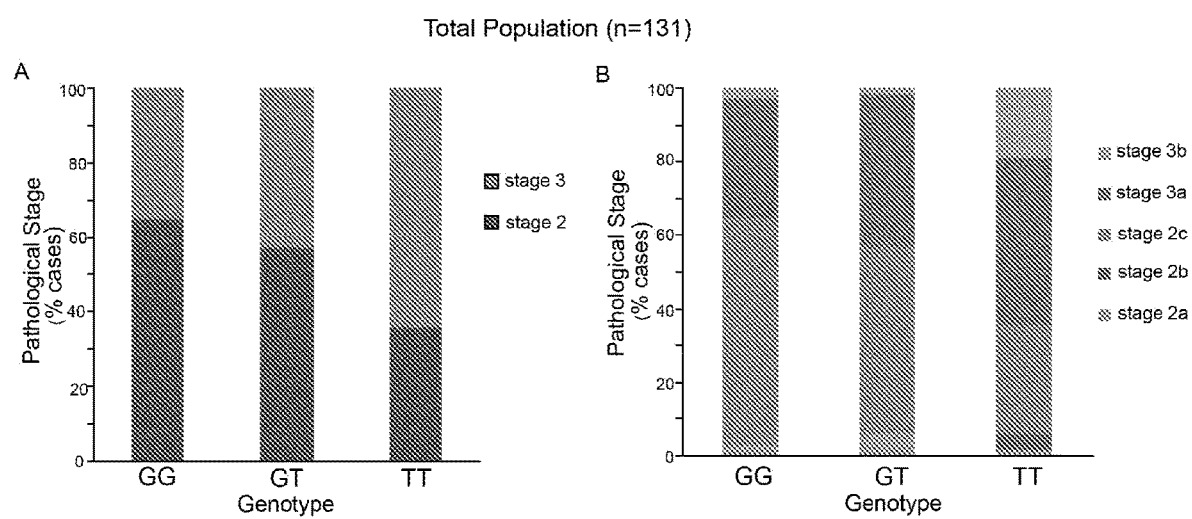
FIG. 9 depicts a comparison of rs13136737 genotypes with the combined pathological stages (A) or with individual stages (B) of patients in the UACC cohort.

The Variant Allele of rs13136737 in Prostate Cancer Patients Associates with a More Aggressive Phenotype To determine the allele frequency at SNP rs13136737 in PCa patients a mixed-race prostate cancer cohort that was treated by radical prostatectomy was examined. The mean patient age is 63.3 years (range 49-80 years) and the distribution of Gleason score is 46.3%<7, 42.7% 7 and 8.6%>7. Selected clinical characteristics are described in Table 1. There was an association in the UACC discovery cohort between the rs13136737 TT-allele and aggressive PCa (Tumor Stage 2 versus Tumor Stage 3; FIG. 4A and FIG. 9) and Gleason Score (FIG. 4B). Individuals with the rs13136737 TT genotype were at significantly higher risk of extraprostatic disease compared to those with the GG genotype (Odds Ratio=3.34, p=0.008, Table 2). Including all possible genotypes in the analysis resulted in a weaker, but still statistically significant, association of the T allele with extraprostatic disease (Odds Ratio=1.87, p=0.006, Table 2). No statistically significant difference in risk of extraprostatic disease between the heterozygous genotype and GG homozygotes was observed (Odds Ratio=3.39, p=0.49).

TABLE 1

Clinical Characteristics of UACC Discovery Prostate Cancer Cohort (N = 133 radical prostatectomy (RP) patients).

| Age at RP (year) = 63.3 | |
|---|---|
| <50 | 1.5% (2) |
| 50-60 | 27.8% (37) |
| 60-70 | 45.8% (61) |
| 70> | 24.8% (33) |
| Race | |
| Caucasian | 77.4% (103) |
| Hispanic | 15.8% (21) |
| African American | 5.3% (7) |
| Other | 1.5% (2) |
| Mean PSA at RP = 7.9 ng/ml | |
| RP Gleason Grade = 6.79 | |
| 3 + 3 | 40.2% (53) |
| 3 + 4 | 35.6% (47) |
| 3 + 5 | 0.7% (1) |
| 4 + 3 | 9.1% (12) |
| >4 + 4 | 14.4% (19) |
| Pathologic Stage | |
| pT2aN0Mx | 3.8% (5) |
| pT2bN0Mx | 1.5% (2) |
| pT2cN0Mx | 45% (59) |
| pT3aN0Mx | 40.5% (53) |
| pT3bN0Mx | 8.4% (11) |
| pT3bN1Mx | 0.8% (1) |

TABLE 2

Analysis of SNP rs13136737 in two independent cohorts: Discovery cohort UACC Mixed Race and an African American validation cohort from dbGaP. Odds ratios refers to Stage 3 versus Stage 2 cancer in the Mixed Race cohort and "Severe" versus "Not-severe" for carriers of the risk allele (T).

| Age Group | <65 | ≥65 | All ages |
|---|---|---|---|
| Mixed race (UACC cohort, TT versus GG) | | | |
| N | 38 | 44 | 82 |
| Odds ratio | 9.78 | 1.50 | 3.34 |
| Odds ratio (2.5%) | 2.06 | 0.40 | 1.36 |
| Odds ratio (97.5%) | 73.05 | 5.57 | 8.60 |
| P-value* | 0.003 | 0.543 | 0.008 |
| Mixed race (UACC cohort, GT and TT versus GG) | | | |
| N | 63 | 68 | 131 |
| Odds ratio | 3.13 | 1.26 | 1.87 |
| Odds ratio (2.5%) | 1.46 | 0.67 | 1.19 |
| Odds ratio (97.5%) | 7.52 | 2.40 | 3.00 |
| P-value* | 0.003 | 0.471 | 0.006 |
| African-Americans (dbGaP) | | | |
| N | 671 | 654 | 1344 |
| Odds ratio | 1.58 | 1.18 | 1.34 |
| Odds ratio (2.5%) | 1.10 | 0.82 | 1.04 |
| Odds ratio (97.5%) | 2.26 | 1.69 | 1.72 |
| P-value* | 0.013 | 0.373 | 0.025 |

*ANOVA vs null model, statistically significant p-values are in bold font.

An interaction between rs13136737 genotype, age and pathological stage was identified. Men less than 65 years old exhibited a strong association between the rs13136737 TT genotype and extraprostatic disease (Odds ratio=9.78, p=0.003, Table 2); in contrast, this association was not seen in older men (Table 2). A strong association with increased risk for the T allele was also observed in younger men when all rs13136737 genotypes (Odds ratio=3.13, p=0.003, Table 2) are included, but, again, there was no association in older men (Table 2).

To verify the potential of rs13136737 as a predictor for more aggressive PCa, a set of logistic regression models using rs13136737 information was generated as well as Gleason Score and age to estimate PCa severity (see Methods). As a single predictor, rs13136737 exhibited good performance as an indicator of severe versus non-severe PCa (AUC=0.63, p=$6.26 \times 10^{-3}$, Table 3). When rs13136737 genotype was combined with Gleason Score, the performance improved (AUC=0.79, p=$8.04 \times 10^{-9}$, Table 3), with further gains achieved when the statistical model was adjusted for age (AUC=0.82, p=$5.85 \times 10^{-10}$, Table 3). These results indicate that rs13136737 has potential to be used as a predictor for severe PCa used alone and in combination with other clinical variables.

TABLE 3

Multivariate Logistic Regression model of Performance of rs13136737 in the prediction of severe versus non-severe PCa for the discovery cohort (UACC).

| | AUC | P-value |
|---|---|---|
| rs136737 | 0.630 | 6.26E−03 |
| Age | 0.689 | 1.26E−04 |
| rs136737 + age | 0.724 | 2.51E−05 |
| Gleason score | 0.761 | 8.32E−09 |
| rs136737 + Gleason | 0.792 | 8.04E−09 |
| rs136737 + Gleason + age | 0.823 | 5.85E−10 |

To validate the results from the UACC discovery cohort, a second independent prostate cancer cohort from the GENEVA Prostate Cancer study was examined. The SNP rs13136737 is genotyped in a small fraction of these prostate cancer patient samples, and available data are all from African-Americans (n=2912, about half PCa patients and half controls). The frequency of the risk allele (T) in this dataset is 13.59%, and is exactly identical between cases and controls (and also similar to allele frequency data from other African-American samples, e.g. FIG. 1), indicating that variation at rs13136737 is not associated with overall risk of PCa development. However, just as observed in the discovery cohort, there is a significant association between the T-allele and risk of more severe PCa in the overall validation dataset (OR=1.34, p=0.025). This association is driven by younger patients (OR=1.58, p=0.013, <65 years); in older patients there is no association between genotype and severe PCa (OR=1.18, p=0.373, ≥65 years).

The similarity between the UACC discovery and GENEVA validation cohorts in terms of a significant association between rs13136737 genotype and risk of severe PCa in younger patients is robust to the difference in racial composition between the groups (mixed-race, mainly Caucasian & Hispanic versus African-American) and the frequency of the risk allele (a much higher frequency of the risk allele in the UACC cohort).

Example 6 miR-367 Expression in Genotyped Prostate Cancer Specimens

Figure 5:
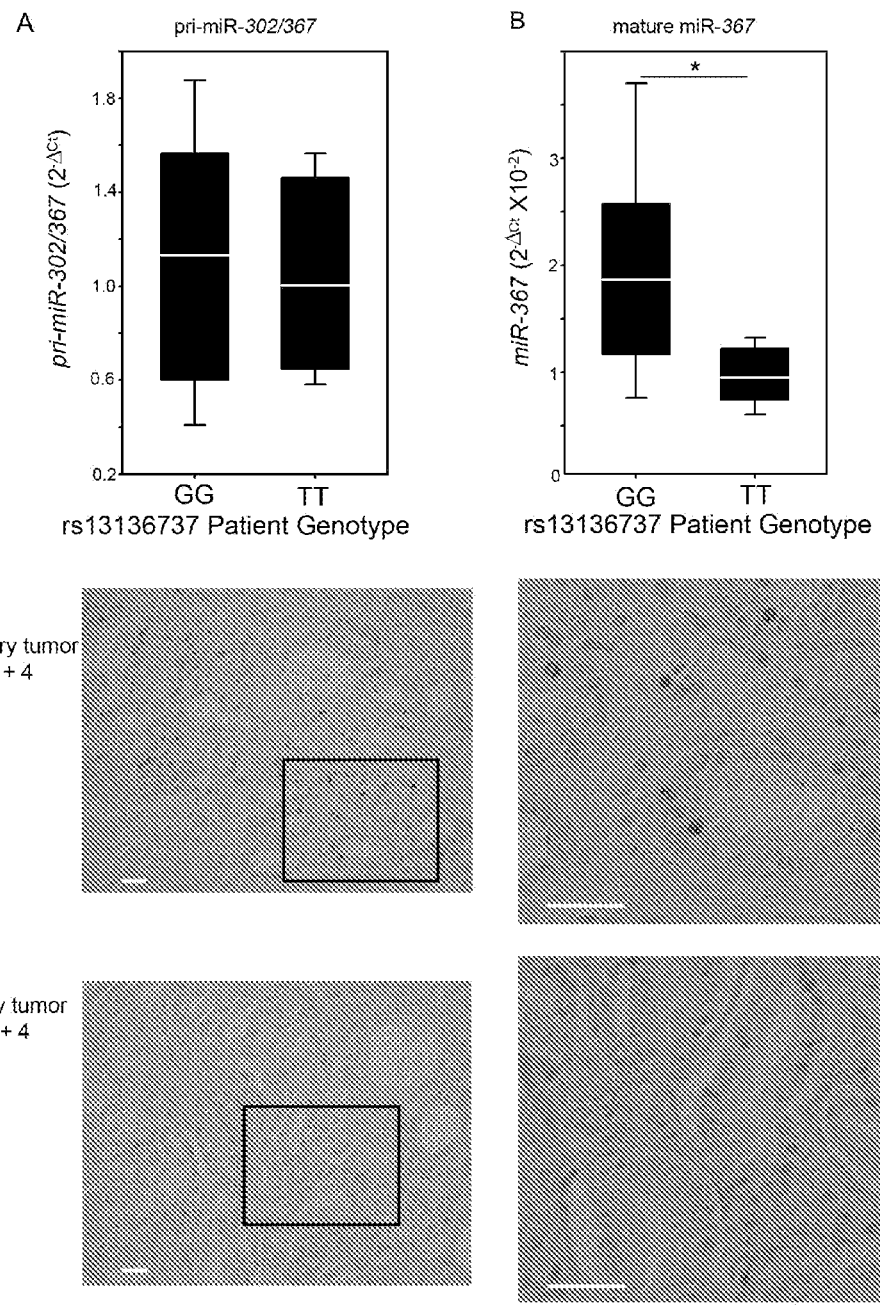
FIG. 5 depicts results of experiments involving genotyped primary cancer tissue specimens that were analyzed by RT-qPCR and in situ hybridization (ISH). The primary miR-302/367 transcript and mature miR-367 levels were quantitated by quantitative PCR to determine expression level. ISH was carried out to identify the localization miR-367 positive cancer cells. (A) Taqman RT-qPCR detection of pri-miR-302/367 in primary cancer specimens from genotyped rs13136737 GG and TT patients. Normalization was performed with RNU6. Values are the mean of at least three independent experiments. Error bars indicate standard deviation. A two-tailed t test was used to compare the expression level of miR-367 in GG and TT genotyped patient specimens. (B) Taqman RT-qPCR detection of mature miR-367-3p in primary cancer specimens from rs13136737 GG and TT patients. (C) miR-367 ISH in the primary specimen for GG-patient (GS 4+4=8; pT3a) (20× and 60×). (D) miR-367 ISH in the primary specimen for TT-patient (GS 3+4=7; pT3a) (20× and 60×). Scale bar=50 μm.

The allele specific differences in the expression level of the miRNAs from the miR-302/367 locus in prostate cancer tissues from genotyped patients was examined (FIG. 5). The level of the pri-miR-302/367 transcript in primary prostate cancer specimens was not statistically different between GG-allele and TT-allele patients (P=0.553). To evaluate the miR-367 expression in terms of abundance and heterogeneity of intratumoral localization genotyped prostate cancer tissue specimens by quantitative real time PCR and in situ hybridization (ISH) was analyzed. The miR-367 expression level in tissue specimens from patients with either the rs13136737 GG- or TT-genotypes were analyzed in two different samples from each tumor specimen by RT-qPCR. Importantly, mature miR-367 showed differential expression levels between the GG-allele and the TT-allele patient genotypes (FIG. 5B). The PCa patient GG-allele tissue samples had elevated miR-367 levels compared to the TT patients.

To characterize the spatial localization of miR-367 in genotyped prostate tissue samples expression by in situ hybridization (ISH) was detected. Formalin-fixed paraffin embedded samples (n=6) with the rs13136737 GG genotype showed overall a higher level of miR-367 positive cells, and there was a greater diversity of expression level than the TT-genotype specimens (n=6). Localization of the miR-367 ISH showed the signal was in individual carcinoma cells and occasionally in clusters. Rarely the miR-367 positive signal was detected in the peritumoral surrounding stromal tissue. The frequency and intensity of miR-367 expression in tumor cells were evaluated in the genotyped samples. The analyzed miR-367 positive tumor cells with the GG genotype showed that 9.0% of tumor cells were strongly labeled (FIG. 5C). In contrast, low intensity miR-367 ISH labeling was positive in a similar number of tumor cells in the TT genotype specimens and strong intensity labeling was present in only a few carcinoma cells per field (FIG. 5D).

Example 7

Figure 6:
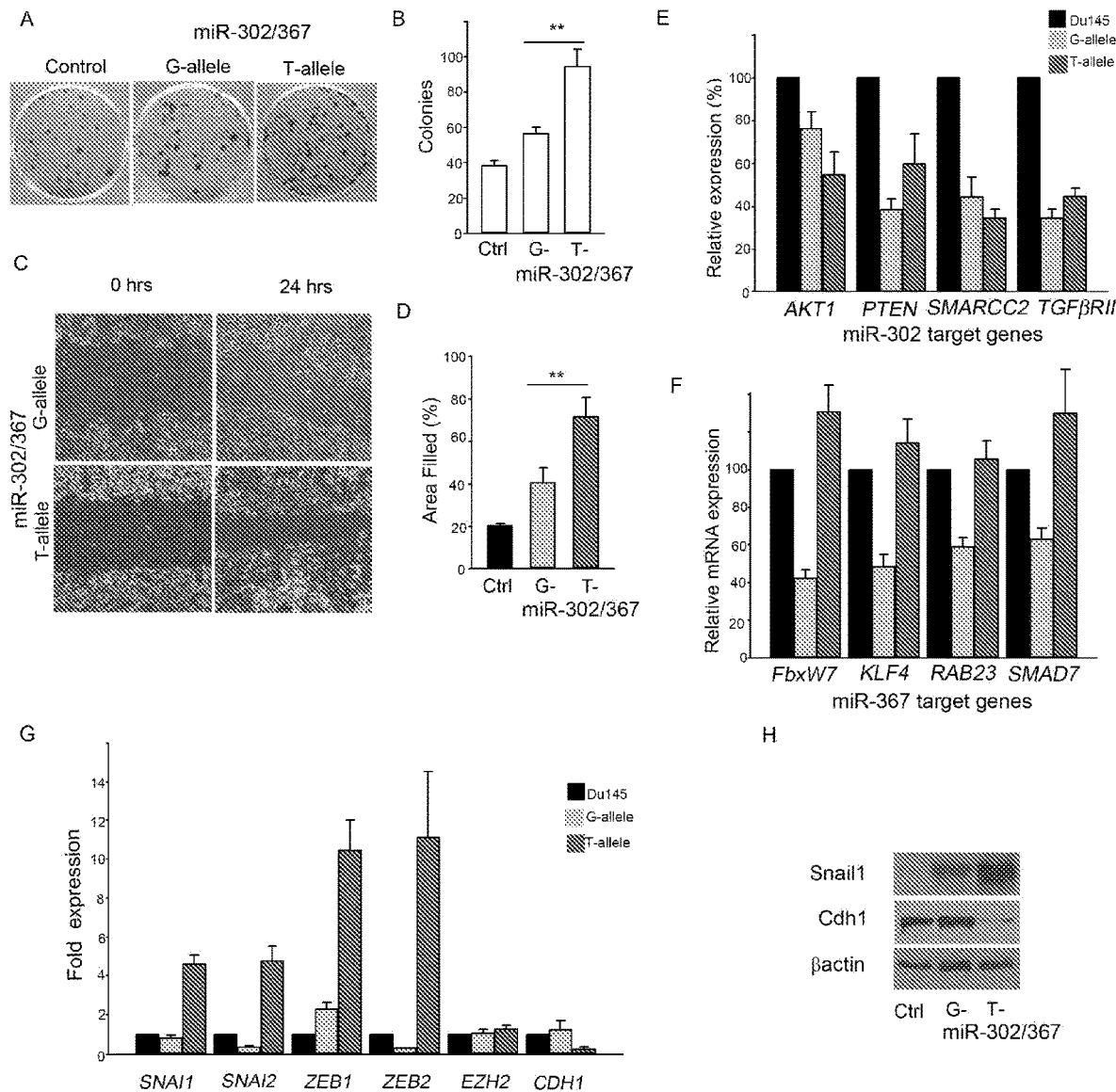
FIG. 6 depicts results of experiments involving the characterization of miR-302/367 G-allele and T-allele cells to determine effects of overexpression on cellular behavior and gene expression levels. (A) clongenic colony formation assays and (B) quantification of colony counts. Wound edge migration for 24 hours was examined by creating a scratch in the epithelial monolayers (C) and migration distance is shown in (D). (E) RT-qPCR analysis of total RNA isolated from Du145 cells or cells over-expressing miR-302/367 G- or T-allele. The validated miR-302 target genes AKT1, PTEN, SMARCC2 and TGFβRII are shown. (F) RT-qPCR analysis of total RNA isolated from Du145 cells or cells over-expressing miR-302/367 G- or T-allele. The validated miR-367 target FbxW7, KLF4, RAB23, and SMAD7 are shown. (G) RT-qPCR analysis of total RNA isolated from Du145 cells or cells over-expressing miR-302/367 G- or T-allele. A set of epithelial mesenchymal transcription factors SNAI1, SNAI2, ZEB1, ZEB2, EZH2 along with CDH1 were analyzed. (H) Immunoblotting for Snail1 and Cdh1 with lysates from control Du145 cells and miR-302/367 G- or T-allele cells.

Overexpression of the miR-302/367 G- or T-Alleles in Prostate Cancer Cells Differentially Affects Cellular Behavior To further characterize the rs13136737 allele specific effects on cellular properties, holoclone assays with Du145 cells overexpressing the miR-302/367 alleles and migration assays were utilized. The behavior of PCa cell holoclones has been reported to reflect self-renewal cancer cells and is shown in FIGS. 6A and 6B. The results showed that clonogenicity and migration were increased in both G-allele and T-allele cells over the vector only control cells. In addition, overexpression of the miR-302/367 T-allele in Du145 cells significantly increased both clonogenic capacity (FIGS. 6C and 6D) and also wound migration of the epithelial population compared to the G-allele cells. Because T-allele cells have reduced levels of miR-367 compared to the G-allele cells (FIG. 2B) these results indicate that the presence of miR-367 negatively regulates migration ability and self-renewal properties.

To evaluate the roles of miR-302/367 allele-specific overexpression on the malignant process, RT-qPCR of selected miR-302 or miR-367 targets was performed. It has been widely demonstrated that miRNAs post-transcriptionally target hundreds of different mRNAs to coordinate the mRNA expression of networks of proteins. There are more than 40 reported direct gene targets of miR-302a,b,c,d and these affect pathways involved in chromatin remodeling, cell cycle regulation, mesenchymal epithelial transition, TGFβ family regulation and the Hippo pathway (Card D A, et al., Mol Cell Biol 2008; 28:6426-38; Li H L, et al., Cell Death Dis 2016; 7:e2078; Tian Y, et al., Sci Transl Med 2015; 7:279ra38; Subramanyam D, et al., Nat Biotechnol 2011; 29:443-8). TGFβRII, SMARCC2, PTEN and AKT1 mRNA levels were significantly reduced in both G-allele and T-allele cells (FIG. 6E and NR2F2 in FIG. 1). The levels of knockdown were similar in cells from both G-allele and T-allele cells. The expression of a variety of miR-367 target genes in cells that overexpress miR-302/367 G- or T-alleles (FIG. 6F) was examined. The invention relates to the idea that only the miR-302/367 G-allele can show inhibition of miR-367 target genes, while cells containing the T-allele transcripts may be unaffected. Genes that are validated direct targets for miR-367 inhibition include SMAD7, Rab23, KLF4 and FBxW7 (Zhu Z, et al., Cancer Sci 2015; 106: 1188-95; Xu J, et al., Oncol Rep 2017; 37:1052-8; Wang G C, et al., J Bone Oncol 2016; 5:51-6). These genes have also been reported to have critical roles in regulating signaling pathways associated with PCa progression including: the TGFβ signaling, hedgehog signaling, androgen receptor axis and the notch pathway, respectively.

To further investigate potential mechanisms associated with the allele-specific differences genes that regulate both differentiation and invasion and metastasis were analyzed. As shown in FIG. 6G transcripts for transcriptional repressors of epithelial differentiation in the miR-302/367 allele-specific cell lines were examined. The miR-302/367 T-allele cells had significantly elevated levels of SNAI1, SNAI1, ZEB1 and ZEB2 which resulted in the reduction of E-cadherin (CDH1) at both the transcript and the protein level (FIGS. 6G and H). Thus, the more aggressive phenotype of the miR-302/367 T-allele cells with increased migration and clonogenicity is at least in part due to the loss of epithelial differentiation and cell-cell adhesion. The set of transcription factors that included SNAI1, SNAI2, TWIST, ZEB1 and ZEB2 were initially identified as regulating epithelial-mesenchymal plasticity in embryonic morphogenesis and subsequently as suppressing CDH1. Their role in cancer progression is built upon ectopic expression of these EMT regulators or correlative analyses of clinical samples. NR2F2 is a positive transcriptional regulator of ZEB1 and ZEB2, but its expression is reduced in the miR-302/367 G- and T-allele cells by miR-302. The molecular basis for the up-regulation has yet to be defined, but suggests that other transcriptional regulators that are miR-367 targets. The miR-302/367 T-allele cells and T-allele patient samples consistently show a less differentiated and more aggressive prostate cancer phenotype.

Example 8

Prostate cancer is heterogeneous in its clinical behavior ranging from indolent disease to aggressive metastatic cancer with rapid mortality. Because localized disease can be effectively treated, the clinical challenge is to identify those cancers that need immediate treatment. Genome-wide association studies (GWAS) have identified >100 genetic risk loci associated with prostate cancer susceptibility (Xu J, et al., Proc Natl Acad Sci USA 2010; 107:2136-40; Al Olama A A, et al., Nat Genet 2014; 46:1103-9; Bensen J T, et al., Prostate 2013; 73:11-22; Schaid D J, et al., Hum Genet 2006; 120:471-85; Berndt S I, et al., Nat Commun 2015; 6:6889). However, despite the progress of GWAS analyses in identification of prostate cancer risk loci few of the markers can distinguish between non-aggressive and aggressive advanced disease. Genetic factors are thought to contribute in part to PCa aggressiveness. For example, studies have shown increased risk of prostate cancer-related death among offspring who have a family history of fatal prostate cancer (Lindstrom L S, et al., Lancet Oncol 2007; 8:1001-6; Hemminki K. World J Urol 2012; 30:143-8).

Studies are emerging that show miRNA dysregulation contributes to multiple aspects of PCa progression including heterogeneity, propagation, invasion and metastasis (Fang Y X, et al., Oncogene 2014; 33:135-47). The role of miRNA function in prostate cancer is further shown by the increased expression of miRNA biogenesis genes (e.g. Dicer and DGCR8) in PCa oncogenesis (Belair C D, et al., EMBO Rep 2015; 16:1219-32; Poliseno L, et al., Sci Signal 2010; 3:ra29). Studies were initiated to better understand molecular mechanisms that regulate aggressive disease, such as a miRNA program that could activate a subpopulation of cells within the primary tumor. The miR-302/367 cluster is not expressed in normal prostate tissue, but is highly expressed in embryonic stem cells, induced pluripotent stem cells, and expression in PCSCs is shown. Thus, dysregulation of miR-302/367 may contribute to PCa initiation and/or progression. Identifying biomarkers that can be utilized in conjunction with clinical prostate cancer diagnosis to distinguish which cancers are likely to require immediate treatment is of critical clinical importance. Because miR-302/367 is expressed in a rare population of cells in healthy adult tissue, these miRNAs are promising biomarkers for cancer detection (e.g., (Murray M J, et al., Am J Clin Pathol 2011; 135:119-25)) and also have potential use as tools for new cancer therapies (e.g. (Lin S L, et al., RNA 2008; 14:2115-24)).

The results indicate that the pri-miR-302/367 SNP rs13136737G/T can serve as a predictive biomarker of disease risk for aggressive PCa. The TT genotype of rs13136737 associates significantly with increased risk for loss of tumor differentiation and expansion beyond the prostate capsule in the mixed ethnic UACC discovery cohort, and this observation was validated in a second independent study of African-American men. In both the discovery and validation datasets the association between aggressive disease and rs13136737 genotype was significant only in men undergoing prostatectomy at a younger age (<65 years), and there was no association in older men in either dataset. The mean age of PCa in men in the US population is 66 years. Studies have reported different pathological characteristic (Gleason score) in younger PCa patients compared to older PCa patients (Kregel S, Kiriluk K J, Rosen A M, Cai Y, Reyes E E, Otto K B, et al. Sox2 is an androgen receptor-repressed gene that promotes castration-resistant prostate cancer. PLoS One 2013; 8:e53701). The result suggests that expression of mature miR-367 is influenced by rs13136737 genotype, and that this may influence risk for aggressive PCa in younger men. The risk allele of rs13136737 is common in worldwide populations, occurring at highest frequencies in Native Americans, intermediate frequencies in Europeans and Asians, and the lowest frequency in Africans and African-Americans.

Microprocessor, Dicer and additional protein accessory factors have multiple roles in processing of polycistronic pri-miRNAs. To understand whether the two alleles of polymorphism rs13136737 are processed to mature miRNAs with equal efficiency, stable cell lines expressing the individual alleles were made. While cells expressing either the GG-allele or the TT-alleles had similar levels of primary transcripts from the miR-302/367 cluster, the rs13136737-TT genotype had reduced expression levels of mature miR-302d and miR-367. The level of other mature miR-302 isoforms (miR-302a, miR-302b and miR-302c) were expressed at normal levels. This patterns suggests an inability of the Drosha-DCGR8 Microprocessor complex to process the cleavage of the primary transcript between miR-302d and miR-367, thus affecting the subsequent processing to mature miRNAs in the cytoplasm by Dicer.

The canonical processing of miRNA primary transcripts to precursor miRNAs is largely dependent on the overall pri-miRNA structure. Microprocessor recognizes the pri-miRNA through stem loop and the stem loop single stranded RNA junction to cleave both 5' and 3' flanking segments to generate pre-miRNAs. The basal junction of a pri-miRNA, where the stem and the flanking unstructured region join is required for processing (Han J, et al., Cell 2006; 125:887-901). It has been proposed that this region serves as an anchoring domain for the Microprocessor to determine the cleavage sites ~11 bp away. Three short sequence motifs have been identified that are important in pri-miRNA processing including a CNNC motif ~17 nucleotides downstream of pri-miRNA hairpins (Auyeung V C, et al., Cell 2013; 152:844-58). This pri-miRNA motif in different subset of miRNAs interacts with SRp20/SRSF3 or the related splicing factor 9G8/SRSF7. Moreover the RNA helicase p72 also binds to this CNNC motif in a distinct set of miRNAs (Mori M, et al., Cell 2014; 156:893-906). For polycistronic pri-miRNAs, such as miR-17~92, efficient biogenesis requires removal of complex secondary structures that are inhibitory and require removal by endonuclease CPSF3 (Du P, et al., Cell 2015; 162:885-99). The palindrome containing rs13136737 overlaps with the CNNC sequence motif between pre-miR-302d and pre-miR-367. Further studies are required to determine the mechanisms that contribute to the reduced processing of the T-allele of rs13136737.

ALDH$^{hi}$ prostate cancer stem cells can express pri-miR-302/367 transcript concomitantly with the transcription factors Sox2, Oct4 and Nanog. There are evolutionarily conserved binding sites for Sox2, Oct4 and Nanog in the miR-302/367 promoter that when occupied activate transcription. These core pluripotency transcription factors also function to repress promoters of developmental genes. The combination of these factors determines the identity of pluripotent stem cells and reduction in their expression levels mediates a shift to a differentiated state. Localization of Sox2 in human prostate tissues showed that it is expressed in normal basal cells (Kregel S, et al., PLoS One 2013; 8:e53701). In tumors Sox2 is widely expressed in a subset of cancers and in the majority of castration resistant PCa metastases. A role for Sox2 is well established in brain, beast, lung, pancreatic and esophageal cancers. The knockdown of Sox2 in tumor initiating cells found in glioblastoma and breast cancers results in inhibition of self-renewal. Previously, Nanog expression in prostate cancer cells was shown to confer both CSC properties such as enhanced clonal growth and self-renewal and androgen independent tumor growth (Jeter C R, et al., Stem Cells 2009; 27:993-1005).

The functions of the miR-302/367 cluster in ESCs include critical roles in regulating cell cycle and apoptosis (Anokye-Danso F, et al., J Cell Sci 2012; 125:4179-87). How the miRNAs in this cluster affect specific gene programs and cancer progression is poorly understood. The miR-302/367 cluster encodes four miR-302-3p family members that are expressed in stem cell populations at different levels and have a conserved seed sequence. There is also redundancy in mRNA targeting by miR-367-3p; the microRNAs miR-25-3p, miR-32-5p and miR-92-3p share the same seed sequence and targets. The miR-302/367 cluster is not expressed in differentiated prostate cancer epithelial cells, but their expression is upregulated in prostate cancer stem cells, which are a subset of the bulk tumor cell population.

Metastasis is a multistep cascade of cellular processes including invasion and dissemination, circulation, and colonization. The majority of the validated miR-302 target mRNAs are transcripts that are in developmental signaling pathways, oncogenes, and chromatin regulators (reviewed in (Anokye-Danso et al., supra)). The results show that pri-miR-302/367 expression in PCSCs is reversible and this could contribute to the plasticity of the metastatic phenotype. The target mRNAs for miR-367 are less well characterized and include the tumor suppressors SMAD7, Rab23, and FbxW7. In this study it was found that cells expressing the miR-302/367 T-allele, and therefore lacking mature miR-367, had a more aggressive cellular phenotype and these cells had undergone a partial EMT. Either through direct or indirect mechanisms these T-allele cells showed up-regulation of the EMT activating transcription factors SNAI1, SNAI2, ZEB1 and ZEB2 with the loss of E-cadherin. Partial EMT has been proposed to contribute to the invasive process of PCa tumor collective cell migration.

Embodiments of the invention relate to allele specific risk for the pri-miR-302/367 SNP rs13136737 in younger patients with prostate cancer. The primary transcript for both alleles are equally expressed in tumor tissue, but the T-allele reduces processing and the level of mature miR-302d and miR-367. This associates with a more aggressive prostate cancer phenotype with higher Gleason sum scores and tumor extension surrounding tissues. The observations described provide a rationale for further study of the strength of allele specific risk for rs13136737 in conjunction with other polymorphisms different indolent from aggressive disease.

Example 9

As described above, the SNP rs13136737 (G/T), which resides in the flanking region of the miR-302/367 pri-miRNA sequence, affects processing and expression of mature miR-367. There are few validated targets for the miR-367, but RYR3 is one of them (Zhang, L. et al., Proc Natl Acad Sci USA 2011, 108, 13653-13658; Chae, Y. S. et al., Anticancer Res 2013, 33, 513-519). Cells with the TT genotype of this SNP produce greatly diminished amounts of mature miR-367. Individuals with this genotype may have a reduced capacity to carry out miR-directed silencing of RYR3, which may lead to a worse prognosis. It is contemplated that the combination of risk-affecting genotypes may be important in cancer risk, and may be the reason that studies of just SNP rs1044129 have been contradictory. Both additive and synergistic effects on risk are possible (Table 5).

TABLE 5

Combinations of SNP genotypes and their predicted effect on cancer risk.

| | | | RYR3 miR-367 Binding(rs1044129) | | |
|---|---|---|---|---|---|
| | | | High Affinity | | Low Affinity |
| | | | A | A | G |
| miR-367 Level | High 367 | G | 1 | 8% | 12 |
| (rs13136737) | | G | 3 | 19 | 27 |
| | Low 367 | T | 2 | 11 | 16 |

The frequency of the rs13136737 miR-367 and rs1044129 RYR3 SNP varies in different populations studied in the 1000 Genomes Project. About ¾ of Latinos and NHW Americans have the low-affinity, high-risk rs1044129 allele in RYR3. The frequencies of the rs13136737 allele which may increase cancer risk by causing low production miR-367 are closer to 60%. Thus, 1% of Mexican ancestry Latinas should have the protective high-miR-367 producing, high-binding genotype at both loci, while another 16% have the low-producing/low-affinity high-risk genotype (Table 5). Experiments are performed to test the association of individual SNPs with cancer stage at presentation. Most individuals are heterozygous for one of the SNPs. Their risk for late stage breast cancer is also assessed.

For the purposes of this study, early stage breast cancer is defined as Stages 1 and 2, and late breast cancer as Stages 3-4. This is similar to other miRNA studies (Arabkheradmand, A et al., Diagnostic pathology 2015, 10, 178; Dong, L. L. et al., Diagnostic pathology 2015, 10, 45), although different separations have been used for various association studies (Al-Alem, U. et al., PloS one 2014, 9, e112916). It is determined whether people with the highest-risk TT/GG genotype for the two SNPs present with advanced stage breast cancer (Stages 3-4) more often than those with lower-risk genotypes using data gathered as part of the ELLA Binational Breast Cancer Study. The ELLA study enrolled women of Mexican ancestry with a diagnosis of invasive breast cancer and asked whether standard and novel tumor markers, which predict an increased incidence and worse prognosis of breast cancer, differ between women in Mexico and Mexican American women living in the U.S. (Martinez, M., et al., Health Care Law Mon 2010, 2, 1040-1048; Martinez, M. E. et al., Journal of immigrant and minority health/Center for Minority Public Health 2013, 15, 234-243; Nodora, J. N. et al., Journal of immigrant and minority health/Center for Minority Public Health 2014). Information about the stage and grade of tumors was collected as part of the trial (Table 6), as were tumor blocks and saliva samples from which DNA has been extracted.

TABLE 6

Stage at breast cancer diagnosis for 1222 ELLA participants.

| Stage | Number of participants (%) |
|---|---|
| 1 | 154 (18.1) |
| 2 | 376 (44.2) |
| 3 | 289 (34.0) |
| 4 | 32 (3.76) |
| Unknown | 371 |

It is determined whether the combination of SNP described herein predict the occurrence of advanced versus early stage breast cancer. One SNP (rs1044129) has been associated with cancer risk and prognosis, but not unequivocally. The second SNP (rs13136737) interacts functionally. This example tests the hypothesis that a known and a novel SNP can influence cancer risk, as assayed by the stage at breast cancer diagnosis.

While Latinas are 26% less likely to get breast cancer than their white counterparts, one in ten Latinas will develop breast cancer in her lifetime (Society, A. C. Cancer facts & figures for hispanics/latinos 2012-2014; Atlanta, Ga., 2012). A Latina with breast cancer is more likely to be diagnosed at a later stage than her white counterpart and more likely to die from her cancer (Society, A. C. Cancer facts & figures for hispanics/latinos 2012-2014; Atlanta, Ga., 2012). These numbers are reflected in the early age and late stage that women from the ELLA Study were diagnosed with breast cancer (Table 6 and Martinez et al., 2010, supra). Indeed, ELLA participants were diagnosed at later stages than the national average (Society, A.C. Cancer facts & figures for hispanics/latinos 2012-2014; Atlanta, Ga., 2012)). Genomic DNA samples from women in this cohort were analyzed for mutations in known and emerging high-penetrance breast cancer genetic risk factors (e.g. BRCA1, BRCA2 and 20 other known breast cancer risk genes). It was found that about 12% of participants carried a mutation in a high-penetrance gene increasing her breast cancer risk. However, since nearly 50% of ELLA participants were younger than age 50 at diagnosis (Martinez et al., 2010, supra) and more than a third were late stage (Table 6), this does not nearly explain the high burden of cancer in this population. In this the genetic analysis of ELLA samples to a pair of interacting SNPs. More work identifying genetic variants that predict cancer risk and prognosis has been done in non-Hispanic Whites (NHW) than ethnic minorities, and in the USA, ethnic minorities are under-represented in clinical trials (Chen, M. S., Jr et al., Cancer 2014, 120 Suppl 7, 1091-1096) and biobanks (Dang, J. H. et al., Journal of community genetics 2014, 5, 313-327). This study is unique in that it evaluates the effects of genetic variants in the ethnic minority Mexican American population. Mexican American populations have significant admixture between European and Native American, contributing to their unique breast cancer risk profile [13,14,17,20-27]. Additionally, Native Americans have a more frequent TT allele than NHW populations, thus studying the admixed Mexican American population inform studies of both of these underserved groups.

Germline DNA from 186 participants in the ELLA Binational Breast Cancer Study has been genotyped for mutations in 20 highly- and moderately-penetrant breast cancer risk genes. This analysis revealed that 12% of participants carry a clear mutation in a highly-penetrant breast cancer risk gene that increases her cancer risk.

Experiments are performed to determine genotypes for the rs1044129 and rs13136737 SNPs in 1222 Mexican American women with breast cancer who participated in the ELLA Binational Breast Cancer Studyw and to test the association of combinations of risk alleles at rs1044129 and rs13136737 with breast cancer stage, testing synergistic, autosomal dominant, co-dominant and recessive interaction models. Sequenom MassARRAY is used to genotype the rs1044129 rs13136737 SNPs in genomic DNA samples from ELLA participants. Genomic DNA is extracted from formalin fixed paraffin embedded tissue sections (QIAamp DNA FFPE Tissue kit) according to the manufacturer (Qiagen). All samples are genotyped using the TaqMan SNP Genotyping assay (Invitrogen/Thermo Fisher) for SNP rs13136737 and rs1044129. Patient DNA samples, positive control samples of known genotype, negative controls, and duplicate samples were randomly analyzed, with 10% duplicates to test both inter- and intra-plate concordance.

Statistical analysis is performed to describe the frequencies of each SNP and their combination in the ELLA Study. It is determined whether the frequency of each SNP is similar to the frequencies found in a Mexican population from Los Angeles and reported as part of the 1000 Genomes Project. This comparison is made using a one-sample chi-square test for each SNP, with the frequencies from the 1000 Genomes Project considered as the null hypothesis. It is determined whether the frequency of each SNP is in Hardy-Weinberg equilibrium (HWE) in the population. Comparison of the observed versus the expected based on HWE performed using a one-sample chi-square test. It is further determined whether there is a higher frequency of low-risk genotypes in either SNP in women diagnosed with early (Stage 1-2) versus late (Stage 3-4) breast cancer in the ELLA Study. The low risk and medium risk (Table 5) are combined and compared with the high risk (orange) and very high risk combinations. The relative risk for late stage breast cancer is computed separately for very high versus low-medium and high versus low-medium by fitting the appropriate indicator variables in a log-binomial model. A log-binomial model is used to directly estimate the relative risk since the prevalence of advanced breast cancer in the ELLA study is not rare. It is determined whether the patterns of association are most consistent with autosomal dominant, co-dominant, or recessive models, or whether there is synergy in the interaction, such that being homozygous for two different high-risk alleles increases risk more than being homozygous for either alone. These analyses are also performed using log-binomial regression with the appropriate definition of the indicator variables. miR-367 levels are measured in the high (GG allele) vs. low expression (TT allele) rs13136737 genotype carriers. This allows one to validate in clinically-relevant patient samples the in vitro measurements showing that rs13136737 affects miR-367 levels.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

2. The method of claim 1, further comprising detecting one or more additional polymorphisms within the miR367 binding site of a miR-367 target gene, wherein the one or more additional polymorphisms are selected from the group consisting of rs554529439, rs3738605, rs779160212, rs190184622, rs552503477, rs376434444, rs564365943, rs184323168, rs782081551, rs782250445, rs773793923, rs531583915, rs777956656, rs531695647, rs534371083, rs754529737, rs536218449, rs376149979, rs547942938, rs779541552, rs4832251, rs377720171, rs761225773, rs764597151, rs769848105, rs541108841, rs562071649, rs369837241, rs186713556, rs778455839, rs749854946, rs114207812, rs750642705, rs545507911, rs866857502, rs373440595, rs367779602, rs750312883, rs770958350, rs376212863, rs189860773, rs2243063, rs751458316, rs368806393, rs549917675, rs568220009, rs545191229, rs143664576, rs562700047, rs762176006, rs778675469, rs866277742, rs761240500, rs549939832, rs187615842, rs1134256, rs747154768, rs567260225, rs182751703, rs776379731, rs112816609, rs766964761, rs62506082, rs202202550, rs73287908, rs192237910, rs184020953, rs555707201, rs374590195, rs747377222, rs1803193, rs765449636, rs760485290, rs533020456, rs755618712, rs367784695, rs184701525, rs374462812, rs531302092, rs947887, rs187964390, rs532880784, rs754041066, rs748046647, rs374026125, rs529132151, rs186709718, rs752535125, rs748425699, rs778937405, rs770459508, rs752637820, rs542637158, rs759581102, rs755829405, rs534758720, rs553103627, rs752056686, rs541423639, rs577895720, rs186358359, rs543402620, rs17002178, and rs558494389.

3. The method of claim 2, wherein the one or more additional polymorphisms are selected from the group consisting of: rs186709718, rs114207812, rs770958350, rs376212863, rs1899860773, rs2243063; rs751458316;

---

---

We claim:

1. A method comprising:
   a) contacting a sample from a subject diagnosed with prostate cancer with one or more reagents for detecting the presence of a TT allele at rs13136737 associated with the miR-302/367 gene;
   b) detecting the presence of said TT allele at rs13136737 using said reagents;
   c) identifying the subject with said TT allele at rs13136737 as having aggressive prostate cancer; and
   d) administering a prostate cancer treatment comprising androgen depravation therapy to said subject with said TT allele at rs13136737.

rs368806393, rs545507911, rs187964390, rs558494389, rs190184622, rs779160212, rs143664576, rs562700047, rs762176006, rs778937405, rs48425699, rs542637158, rs754041066 and rs755829405.

4. The method of claim 1, wherein the sample is selected from a blood, saliva or buccal swab, or tumor tissue.

5. A method of detecting the presence of polymorphisms, comprising: a) contacting a sample from a subject with one or more reagents for detecting the presence of a GG polymorphism at rs1044129 and a TT polymorphism at rs13136737; and b) detecting the presence of said polymorphisms using said reagents.

6. The method of claim 5, wherein said sample is a breast tissue sample.

\* \* \* \* \*

SEQUENCE LISTING

<160> NUMBER OF SEQ ID NOS: 1

<210> SEQ ID NO 1
<211> LENGTH: 198
<212> TYPE: RNA
<213> ORGANISM: homo sapiens

<400> SEQUENCE: 1
ccucuacuuu aacauggagg cacuugcugu gacaugacaa aaauaagucu uccauguuug      60
aguguggugg uuccuaccua aucagcaauu gcaguuaacg cccacacugu gugcaguucu     120
uggcuacagg ccauuacugu ugcuaauaug caacucuguu gaauauaaau uggaauugca     180
cuuuagcaau ggugaugg                                                  198